(12) United States Patent
Bleck et al.

(10) Patent No.: US 8,398,977 B2
(45) Date of Patent: Mar. 19, 2013

(54) RAGE FUSION PROTEINS

(75) Inventors: Gregory T. Bleck, Cross Plains, WI (US); David M. Hilbert, Bethesda, MD (US)

(73) Assignee: Galactica Pharmaceuticals, Inc., Villanova, PA (US)

( * ) Notice: Subject to any disclaimer, the term of this patent is extended or adjusted under 35 U.S.C. 154(b) by 262 days.

(21) Appl. No.: 12/664,111

(22) PCT Filed: Jun. 13, 2008

(86) PCT No.: PCT/US2008/066956
§ 371 (c)(1),
(2), (4) Date: Jul. 30, 2010

(87) PCT Pub. No.: WO2008/157378
PCT Pub. Date: Dec. 24, 2008

(65) Prior Publication Data
US 2010/0291081 A1 Nov. 18, 2010

Related U.S. Application Data

(60) Provisional application No. 60/943,994, filed on Jun. 14, 2007.

(51) Int. Cl.
*A61K 39/395* (2006.01)
*C12P 21/04* (2006.01)
(52) U.S. Cl. .............................. 424/134.1; 530/387.3
(58) Field of Classification Search .................. None
See application file for complete search history.

(56) References Cited

U.S. PATENT DOCUMENTS

| | | | |
|---|---|---|---|
| 5,656,261 | A | 8/1997 | Cerami et al. |
| 5,819,341 | A | 10/1998 | Simantob et al. |
| 5,853,703 | A | 12/1998 | Cerami et al. |
| 5,864,018 | A | 1/1999 | Morser et al. |
| 6,007,865 | A | 12/1999 | Cerami et al. |
| 6,380,165 | B1 | 4/2002 | Al-Abed et al. |
| 6,440,749 | B1 | 8/2002 | Cerami et al. |
| 6,465,422 | B1 | 10/2002 | Schmidt et al. |
| 6,706,683 | B1 | 3/2004 | Seto et al. |
| 6,790,443 | B2 | 9/2004 | Stern et al. |
| 6,825,164 | B1 | 11/2004 | Stern et al. |
| 7,470,521 | B2 | 12/2008 | O'Keefe et al. |
| 7,485,697 | B2 | 2/2009 | Yamamoto et al. |
| 7,510,843 | B2 | 3/2009 | Roecklin et al. |
| 2001/0039256 | A1 | 11/2001 | Stern et al. |
| 2001/0053357 | A1 | 12/2001 | Stern et al. |
| 2002/0002203 | A1 | 1/2002 | Rahbar |
| 2002/0006391 | A1 | 1/2002 | Smith et al. |
| 2002/0013256 | A1 | 1/2002 | Rahbar et al. |
| 2002/0022234 | A1 | 2/2002 | Al-Abed et al. |
| 2002/0037496 | A1 | 3/2002 | Jacobson et al. |
| 2002/0077293 | A1 | 6/2002 | Cahoon et al. |
| 2002/0082273 | A1 | 6/2002 | Bush et al. |
| 2002/0086282 | A1 | 7/2002 | Pillarisetti et al. |
| 2002/0102604 | A1 | 8/2002 | Edwards et al. |
| 2002/0106726 | A1 | 8/2002 | Schmidt et al. |
| 2002/0116725 | A1 | 8/2002 | Stern et al. |
| 2002/0122799 | A1 | 9/2002 | Stern et al. |
| 2005/0033017 | A1 | 2/2005 | Yamamoto et al. |
| 2006/0030527 | A1 | 2/2006 | Mjalli et al. |
| 2006/0057679 | A1 | 3/2006 | O'Keefe et al. |
| 2006/0078562 | A1 | 4/2006 | Mjalli et al. |
| 2006/0121604 | A1 | 6/2006 | Handa et al. |
| 2006/0140933 | A1 | 6/2006 | Pittman et al. |
| 2008/0199467 | A1 | 8/2008 | Mjalli et al. |
| 2008/0207499 | A1 | 8/2008 | Barile et al. |

FOREIGN PATENT DOCUMENTS

| | | |
|---|---|---|
| EP | 1219639 A1 | 7/2002 |
| WO | WO-9406476 A1 | 3/1994 |
| WO | WO-9410308 A1 | 5/1994 |
| WO | WO-9726913 A1 | 7/1997 |
| WO | WO-9739121 A1 | 10/1997 |
| WO | WO-9739125 A1 | 10/1997 |
| WO | WO-9822138 A1 | 5/1998 |
| WO | WO-9840071 A1 | 9/1998 |
| WO | WO-9907402 A1 | 2/1999 |
| WO | WO-9918987 A1 | 4/1999 |
| WO | WO-9945907 A2 | 9/1999 |
| WO | WO-9954485 A1 | 10/1999 |
| WO | WO-0018970 A1 | 4/2000 |
| WO | WO-0020458 A1 | 4/2000 |
| WO | WO-0020621 A1 | 4/2000 |
| WO | WO-0105422 A2 | 1/2001 |
| WO | WO-0112598 A2 | 2/2001 |
| WO | WO-0118060 A1 | 3/2001 |
| WO | WO-0129269 A2 | 4/2001 |
| WO | WO-0162905 A2 | 8/2001 |
| WO | WO-0176584 A2 | 10/2001 |
| WO | WO-0179849 A2 | 10/2001 |
| WO | WO-0186002 A2 | 11/2001 |
| WO | WO-0192210 A1 | 12/2001 |
| WO | WO-0192892 A2 | 12/2001 |
| WO | WO-0208272 A2 | 1/2002 |
| WO | WO-0212345 A2 | 2/2002 |
| WO | WO-0214519 A1 | 2/2002 |
| WO | WO-0229072 A2 | 4/2002 |

(Continued)

OTHER PUBLICATIONS

Harris et al., "Coupling complement regulators to immunoglobulin domains generates effective anti-complement reagents with extended half-life in vivo," Clin. Exp. Immunol., vol. 129, pp. 198-207 (2002).

(Continued)

*Primary Examiner* — Gregory S Emch

(74) *Attorney, Agent, or Firm* — Buchanan, Ingersoll & Rooney PC

(57) ABSTRACT

The present invention provides novel therapeutics and methods of treatment for diseases associated with activation of the advanced glycation endproducts receptor (RAGE).

9 Claims, 21 Drawing Sheets

FOREIGN PATENT DOCUMENTS

| | | |
|---|---|---|
| WO | WO-0230889 A2 | 4/2002 |
| WO | WO-02066978 A2 | 8/2002 |
| WO | WO-02068636 A1 | 9/2002 |
| WO | WO-2004/016229 A2 | 2/2004 |
| WO | WO-2006036922 A2 | 4/2006 |
| WO | WO-2007011606 A2 | 1/2007 |
| WO | WO-2007024715 A2 | 3/2007 |
| WO | WO-2007130302 A2 | 11/2007 |
| WO | WO-2007146968 A2 | 12/2007 |
| WO | WO-2008100470 A2 | 8/2008 |
| WO | WO-2008137552 A2 | 11/2008 |
| WO | WO-2008153957 A1 | 12/2008 |

OTHER PUBLICATIONS

Weinblatt et al., "A Trial of Etanercept, a Recombinant Tumor Necrosis Factor Receptor:Fc Fusion Protein, in Patients with Rheumatoid Arthritis Receiving Methotrexate," The New England Journal of Medicine, vol. 340(4), pp. 253-259 (1999).

Huttunen et al., "Receptor for advanced glycation end products-binding COOh-terminal motif of amphoterin inhibits invasive migration and metastasis," Cancer Research, vol. 62(16), pp. 4805-4811 (2002).

Stern et al., "Receptor for advanced glycation endproducts (RAGE) and the complications of diabetes," Ageing Research Reviews, vol. 1(1), pp. 1-15 (2002).

Peppel et al., "A tumor necrosis factor (TNF) receptor-IgG heavy chain chimeric protein as a bivalent antagonist of TNF activity". J Exp Med., vol. 174(6), pp. 1483-1489 (Dec. 1, 1991).

Du Yan, S. et al., "Amyloid-$\beta$ peptide-Receptor for Advanced Glycation Endproduct interaction elicits neuronal expression of macrophage-colony stimulating factor: A Proinflammatory pathway in Alzheimer disease", Proc. Natl. Acad. Sci. USA, vol. 94, pp. 5296-5301(1997).

Hori, et al., "The Receptor for Advanced Glycation End Products (RAGE) is a Cellular Binding Site for Amphotenin", The Journal of Biological Chemistry, vol. 270, No. 43, pp. 25752-25761 (1995).

Li, J., et al., "Sp1-binding Elements in the Promoter of RAGE are Essential for Amphoterin-mediated Gene Expression in Cultured Neuroblastoma Cells", The Journal of Biological Chemistry, vol. 273, No. 47, pp. 30870-30878 (1998).

Schmidt, A., et al., "Receptor for Advanced Glycation End Products (AGEs) has a central role in vessel wall interactions and gene activation in response to circulating AGE proteins", Proc. Natl. Acad.Sci. USA, vol. 91, pp. 8807-8811 (1994).

Tanaka, et al., "The Receptor for Advanced Glycation End Products is Induced by the Glycation Products Themselves and Tumor Necrosis Factor-$\alpha$ through Nuclear Factor-kB, and by 17$\beta$-Estradiol through Sp-1 in Human Vascular Endothelial Cells", The Journal of Biological Chemistry, vol. 275, No. 33, pp. 25781-25790 (2000).

Wautier, et al., "Receptor-mediated Endothelial Cell Dysfunction in Diabetic Vasculopathy. Soluable Receptor for Advanced Glycation End Products Blocks Hyperpermeability in Diabetic Rats", J. Clin. Invest., vol. 97, No. 1, pp. 238-243 (1996).

Mickle, et al, "Genotype-phenotype Relationships in Cystic Fibrosis", Med. Clin. North Am., vol. 84, No. 3, pp. 597-607 (2000).

Yan, et al., "Two-amino Acid Molecular Switch in an Epithelial Morphogen that Regulates Binding to Two Distinct Receptors", Science, vol. 290, pp. 523-527 (2000).

Schmidt, AM, et al., "The Multiligand Receptor RAGE as a Progression Factor Amplifying Immune and Inflammatory Responses", J. Clin. Invest., vol. 108, No. 7, pp. 949-955 (2001).

SEQUENCE LISTING

<160> NUMBER OF SEQ ID NOS: 11

<210> SEQ ID NO 1
<211> LENGTH: 2016
<212> TYPE: DNA
<213> ORGANISM: Homo sapiens

<400> SEQUENCE: 1

| | |
|---|---|
| atggcagccg aacagcagt tggagcctgg gtgctggtcc tcagtctgtg gggggcagta | 60 |
| gtaggtgctc aaaacatcac agcccggatt ggcgagccac tggtgctgaa gtgtaagggg | 120 |
| gcccccaaga aaccacccca gcggctggaa tggaaactga acacaggccg gacagaagcc | 180 |
| tggaaggtcc tgtctcccca gggaggaggc ccctgggaca gtgtggctcg tgtccttccc | 240 |
| aacggctccc tcttccttcc ggctgtcggg atccaggatg aggggatttt ccggtgccag | 300 |
| gcaatgaaca ggaatggaaa ggagaccaag tccaactacc gagtccgtgt ctaccagatt | 360 |
| cctgggaagc cagaaattgt agattctgcc tctgaactca cggctggtgt tcccaataag | 420 |
| gtggggacat gtgtgtcaga gggaagctac cctgcaggga ctcttagctg gcacttggat | 480 |
| gggaagcccc tggtgccgaa tgagaaggga gtatctgtga aggaacagac caggagacac | 540 |
| cctgagacag ggctcttcac actgcagtcg gagctaatgg tgaccccagc ccggggagga | 600 |
| gatcccgtc ccaccttctc ctgtagcttc agcccaggcc ttccccgaca ccgggccttg | 660 |
| cgcacagccc ccatccagcc ccgtgtctgg gagcctgtgc ctctggagga ggtccaattg | 720 |
| gtggtggagc cagaaggtgg agcagtagct cctggtggaa ccgtaaccct gacctgtgaa | 780 |
| gtccctgccc agccctctcc tcaaatccac tggatgaagg atggtgtgcc cttgcccctt | 840 |
| cccccccagcc ctgtgctgat cctccctgag atagggcctc aggaccaggg aacctacagc | 900 |
| tgtgtggcca cccattccag ccacgggccc aggaaagcc gtgctgtcag catcagcatc | 960 |
| atcgaaccag gcgaggaggg gccaactgca ggctctgtgg gaggatcagg gctgggaact | 1020 |
| ctagccctgg ccgcttccac caagggccca tccgtcttcc ccctggcgcc ctgctccagg | 1080 |
| agcacctccg agagcacagc cgccctgggc tgcctggtca aggactactt ccccgaaccg | 1140 |
| gtgacggtgt cgtggaactc aggcgccctg accagcggcg tgcacacctt cccggctgtc | 1200 |
| ctacagtcct caggactcta ctccctcagc agcgtggtga ccgtgccctc agcagcttg | 1260 |
| ggcacgaaga cctacacctg caacgtagat cacaagccca gcaacaccaa ggtggacaag | 1320 |
| agagttgagt ccaaatatgg tcccccatgc ccatcatgcc cagcacctga gttcctgggg | 1380 |
| ggaccatcag tcttcctgtt ccccccaaaa cccaaggaca ctctcatgat ctcccggacc | 1440 |
| cctgaggtca cgtgcgtggt ggtggacgtg agccaggaag accccgaggt ccagttcaac | 1500 |
| tggtacgtgg atggcgtgga ggtgcataat gccaagacaa agccgcggga ggagcagttc | 1560 |
| aacagcacgt accgtgtggt cagcgtcctc accgtcctgc accaggactg gctgaacggc | 1620 |
| aaggagtaca agtgcaaggt ctccaacaaa ggcctcccgt cctccatcga gaaaaccatc | 1680 |
| tccaaagcca aagggcagcc ccgagagcca caggtgtaca ccctgccccc atcccaggag | 1740 |
| gagatgacca agaaccaggt cagcctgacc tgcctggtca aaggcttcta ccccagcgac | 1800 |
| atcgccgtgg agtgggagag caatgggcag ccggagaaca actacaagac cacgcctccc | 1860 |
| gtgctggact ccgacggctc cttcttcctc tacagcaggc taaccgtgga caagagcagg | 1920 |
| tggcaggagg ggaatgtctt ctcatgctcc gtgatgcatg aggctctgca caaccactac | 1980 |
| acacagaaga gcctctccct gtctctcggg aaatga | 2016 |

```
<210> SEQ ID NO 2
<211> LENGTH: 671
<212> TYPE: PRT
<213> ORGANISM: Homo sapiens

<400> SEQUENCE: 2

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Ser Thr Lys Gly Pro Ser Val
            340                 345                 350

Phe Pro Leu Ala Pro Cys Ser Arg Ser Thr Ser Glu Ser Thr Ala Ala
    355                 360                 365

Leu Gly Cys Leu Val Lys Asp Tyr Phe Pro Glu Pro Val Thr Val Ser
370                 375                 380
```

```
Trp Asn Ser Gly Ala Leu Thr Ser Gly Val His Thr Phe Pro Ala Val
385                 390                 395                 400
Leu Gln Ser Ser Gly Leu Tyr Ser Leu Ser Val Val Thr Val Pro
            405                 410                 415
Ser Ser Ser Leu Gly Thr Lys Thr Tyr Thr Cys Asn Val Asp His Lys
            420                 425                 430
Pro Ser Asn Thr Lys Val Asp Lys Arg Val Glu Ser Lys Tyr Gly Pro
            435                 440                 445
Pro Cys Pro Ser Cys Pro Ala Pro Glu Phe Leu Gly Gly Pro Ser Val
        450                 455                 460
Phe Leu Phe Pro Pro Lys Pro Lys Asp Thr Leu Met Ile Ser Arg Thr
465                 470                 475                 480
Pro Glu Val Thr Cys Val Val Val Asp Val Ser Gln Glu Asp Pro Glu
                485                 490                 495
Val Gln Phe Asn Trp Tyr Val Asp Gly Val Glu Val His Asn Ala Lys
            500                 505                 510
Thr Lys Pro Arg Glu Glu Gln Phe Asn Ser Thr Tyr Arg Val Val Ser
            515                 520                 525
Val Leu Thr Val Leu His Gln Asp Trp Leu Asn Gly Lys Glu Tyr Lys
530                 535                 540
Cys Lys Val Ser Asn Lys Gly Leu Pro Ser Ser Ile Glu Lys Thr Ile
545                 550                 555                 560
Ser Lys Ala Lys Gly Gln Pro Arg Glu Pro Gln Val Tyr Thr Leu Pro
                565                 570                 575
Pro Ser Gln Glu Glu Met Thr Lys Asn Gln Val Ser Leu Thr Cys Leu
            580                 585                 590
Val Lys Gly Phe Tyr Pro Ser Asp Ile Ala Val Glu Trp Glu Ser Asn
            595                 600                 605
Gly Gln Pro Glu Asn Asn Tyr Lys Thr Thr Pro Pro Val Leu Asp Ser
        610                 615                 620
Asp Gly Ser Phe Phe Leu Tyr Ser Arg Leu Thr Val Asp Lys Ser Arg
625                 630                 635                 640
Trp Gln Glu Gly Asn Val Phe Ser Cys Ser Val Met His Glu Ala Leu
                645                 650                 655
His Asn His Tyr Thr Gln Lys Ser Leu Ser Leu Ser Leu Gly Lys
            660                 665                 670

<210> SEQ ID NO 3
<211> LENGTH: 2037
<212> TYPE: DNA
<213> ORGANISM: Homo sapiens

<400> SEQUENCE: 3
atggcagccg aacagcagt tggagcctgg gtgctggtcc tcagtctgtg gggggcagta      60
gtaggtgctc aaaacatcac agcccggatt ggcgagccac tggtgctgaa gtgtaagggg     120 gccccccaaga aaccacccca gcggctggaa tggaaactga acacaggccg acagaagcc     180 tggaaggtcc tgtctcccca gggaggaggc ccctgggaca gtgtggctcg tgtccttccc     240
aacggctccc tcttccttcc ggctgtcggg atccaggatg aggggatttt ccggtgccag     300
gcaatgaaca ggaatggaaa ggagaccaag tccaactacc gagtccgtgt ctaccagatt     360
cctgggaagc cagaaattgt agattctgcc tctgaactca cggctggtgt tcccaataag     420
gtggggacat gtgtgtcaga gggaagctac cctgcaggga ctcttagctg gcacttggat     480
gggaagcccc tggtgccgaa tgagaaggga gtatctgtga aggaacagac caggagacac     540
```

```
cctgagacag ggctcttcac actgcagtcg gagctaatgg tgaccccagc ccggggagga      600
gatcccgtc ccaccttctc ctgtagcttc agcccaggcc ttccccgaca ccgggccttg      660
cgcacagccc ccatccagcc ccgtgtctgg gagcctgtgc ctctggagga ggtccaattg      720
gtggtggagc cagaaggtgg agcagtagct cctggtggaa ccgtaaccct gacctgtgaa      780
gtccctgccc agccctctcc tcaaatccac tggatgaagg atggtgtgcc cttgcccctt      840
cccccagcc ctgtgctgat cctccctgag atagggcctc aggaccaggg aacctacagc      900
tgtgtggcca cccattccag ccacgggccc caggaaagcc gtgctgtcag catcagcatc      960
atcgaaccag gcgaggaggg gccaactgca ggctctgtgg gaggatcagg gctgggaact     1020
ctagccctgg ccggtagcgg ctccggaagt ggggcttcca ccaagggccc atccgtcttc     1080
cccctggcgc cctgctccag gagcacctcc gagagcacag ccgccctggg ctgcctggtc     1140
aaggactact tccccgaacc ggtgacggtg tcgtggaact caggcgccct gaccagcggc     1200
gtgcacacct tccggctgt cctacagtcc tcaggactct actccctcag cagcgtggtg     1260
accgtgccct ccagcagctt gggcacgaag acctacacct gcaacgtaga tcacaagccc     1320
agcaacacca aggtggacaa gagagttgag tccaaatatg gtccccatg ccatcatgc      1380
ccagcacctg agttcctggg gggaccatca gtcttcctgt tccccccaaa acccaaggac     1440
actctcatga tctcccggac ccctgaggtc acgtgcgtgg tggtggacgt gagccaggaa     1500
gaccccgagg tccagttcaa ctggtacgtg gatggcgtgg aggtgcataa tgccaagaca     1560
aagccgcggg aggagcagtt caacagcacg taccgtgtgg tcagcgtcct caccgtcctg     1620
caccaggact ggctgaacgg caaggagtac aagtgcaagg tctccaacaa aggcctcccg     1680
tcctccatcg agaaaaccat ctccaaagcc aaagggcagc cccgagagcc acaggtgtac     1740
accctgcccc catcccagga ggagatgacc aagaaccagg tcagcctgac ctgcctggtc     1800
aaaggcttct accccagcga catcgccgtg gagtgggaga gcaatgggca gccggagaac     1860
aactacaaga ccacgcctcc cgtgctggac tccgacggct ccttcttcct ctacagcagg     1920
ctaaccgtgg acaagagcag gtggcaggag gggaatgtct tctcatgctc cgtgatgcat     1980
gaggctctgc acaaccacta cacacagaag agcctctccc tgtctctcgg gaaatga       2037
```

<210> SEQ ID NO 4
<211> LENGTH: 678
<212> TYPE: PRT
<213> ORGANISM: Homo sapiens

<400> SEQUENCE: 4

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
```

-continued

```
                115                 120                 125
Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Gly Ser Gly Ser Gly Ser Gly Ala
            340                 345                 350

Ser Thr Lys Gly Pro Ser Val Phe Pro Leu Ala Pro Cys Ser Arg Ser
        355                 360                 365

Thr Ser Glu Ser Thr Ala Ala Leu Gly Cys Leu Val Lys Asp Tyr Phe
    370                 375                 380

Pro Glu Pro Val Thr Val Ser Trp Asn Ser Gly Ala Leu Thr Ser Gly
385                 390                 395                 400

Val His Thr Phe Pro Ala Val Leu Gln Ser Ser Gly Leu Tyr Ser Leu
                405                 410                 415

Ser Ser Val Val Thr Val Pro Ser Ser Ser Leu Gly Thr Lys Thr Tyr
            420                 425                 430

Thr Cys Asn Val Asp His Lys Pro Ser Asn Thr Lys Val Asp Lys Arg
        435                 440                 445

Val Glu Ser Lys Tyr Gly Pro Pro Cys Pro Ser Cys Pro Ala Pro Glu
    450                 455                 460

Phe Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser Gln Glu Asp Pro Glu Val Gln Phe Asn Trp Tyr Val Asp Gly
            500                 505                 510

Val Glu Val His Asn Ala Lys Thr Lys Pro Arg Glu Glu Gln Phe Asn
        515                 520                 525

Ser Thr Tyr Arg Val Val Ser Val Leu Thr Val Leu His Gln Asp Trp
    530                 535                 540
```

| | | | | | | | | | | | | | |
|---|---|---|---|---|---|---|---|---|---|---|---|---|---|
|Leu|Asn|Gly|Lys|Glu|Tyr|Lys|Cys|Lys|Val|Ser|Asn|Lys|Gly|Leu|Pro|
|545| | | | |550| | | | |555| | | | |560|

```
Leu Asn Gly Lys Glu Tyr Lys Cys Lys Val Ser Asn Lys Gly Leu Pro
545                 550                 555                 560

Ser Ser Ile Glu Lys Thr Ile Ser Lys Ala Lys Gly Gln Pro Arg Glu
                565                 570                 575

Pro Gln Val Tyr Thr Leu Pro Pro Ser Gln Glu Glu Met Thr Lys Asn
            580                 585                 590

Gln Val Ser Leu Thr Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Arg
625                 630                 635                 640

Leu Thr Val Asp Lys Ser Arg Trp Gln Glu Gly Asn Val Phe Ser Cys
                645                 650                 655

Ser Val Met His Glu Ala Leu His Asn His Tyr Thr Gln Lys Ser Leu
            660                 665                 670

Ser Leu Ser Leu Gly Lys
        675

<210> SEQ ID NO 5
<211> LENGTH: 2016
<212> TYPE: DNA
<213> ORGANISM: Homo sapiens

<400> SEQUENCE: 5
atggcagccg aacagcagt tgagcctgg gtgctggtcc tcagtctgtg gggggcagta      60
gtaggtgctc aaaacatcac agcccggatt ggcgagccac tggtgctgaa gtgtaagggg    120
gcccccaaga acccacccca gcggctggaa tggaaactga cacaggccg acagaagct     180 tggaaggtcc tgtctcccca gggaggaggc cctgggaca gtgtggctcg tgtccttccc    240
aacggctccc tcttccttcc ggctgtcggg atccaggatg aggggatttt ccggtgccag   300
gcaatgaaca ggaatggaaa ggagaccaag tccaactacc gagtccgtgt ctaccagatt   360
cctgggaagc agaaattgt agattctgcc tctgaactca cggctggtgt tcccaataag   420
gtggggacat gtgtgtcaga gggaagctac cctgcaggga ctcttagctg gcacttggat   480
gggaagcccc tggtgccgaa tgagaaggga gtatctgtga aggaacagac caggagacac   540
cctgagacag ggctcttcac actgcagtcg gagctaatgg tgaccccagc ccggggagga   600
gatccccgtc ccaccttctc ctgtagcttc agcccaggcc ttcccgacg ccgggccttg    660 cacacagccc ccatccagcc ccgtgtctgg agcctgtgc ctctggagga ggtccaattg    720
gtggtggagc cagaaggtgg agcagtagct cctggtggaa ccgtaaccct gacctgtgaa   780
gtccctgccc agccctctcc tcaaatccac tggatgaagg atggtgtgcc cttgccccct   840 cccccagcc ctgtgctgat cctccctgag atagggcctc aggaccaggg aacctacagc   900
tgtgtggcca cccattccag ccacgggccc caggaaagcc gtgctgtcag catcagcatc   960
atcgaaccag gcgaggaggg gccaactgca ggctctgtgg gaggatcagg gctgggaact  1020
ctagccctgg ccgcttccac caagggccca tccgtcttcc ccctggcgcc ctgctccagg  1080
agcacctccg agagcacagc cgccctgggc tgcctggtca aggactactt ccccgaaccg  1140
gtgacggtgt cgtggaactc aggcgccctg accagcggcg tgcacacctt ccggctgtc   1200 ctacagtcct caggactcta ctccctcagc agcgtggtga ccgtgccctc agcagcttg   1260 ggcacgaaga cctacacctg caacgtagat cacaagccca gcaacaccaa ggtggacaag  1320
agagttgagt ccaaatatgg tccccccatgc ccatcatgcc cagcacctga gttcctgggg  1380
```

```
ggaccatcag tcttcctgtt ccccccaaaa cccaaggaca ctctcatgat ctcccggacc    1440
cctgaggtca cgtgcgtggt ggtggacgtg agccaggaag accccgaggt ccagttcaac    1500
tggtacgtgg atggcgtgga ggtgcataat gccaagacaa agccgcggga ggagcagttc    1560
aacagcacgt accgtgtggt cagcgtcctc accgtcctgc accaggactg gctgaacggc    1620
aaggagtaca agtgcaaggt ctccaacaaa ggcctcccgt cctccatcga aaaaccatc     1680 tccaaagcca aagggcagcc ccgagagcca caggtgtaca ccctgccccc atcccaggag    1740
gagatgacca gaaccaggt cagcctgacc tgcctggtca aaggcttcta ccccagcgac     1800
atcgccgtgg agtgggagag caatgggcag ccggagaaca actacaagac cacgcctccc    1860
gtgctggact ccgacggctc cttcttcctc tacagcaggc taaccgtgga caagagcagg    1920
tggcaggagg ggaatgtctt ctcatgctcc gtgatgcatg aggctctgca caaccactac    1980
acacagaaga gcctctccct gtctctcggg aaatga                              2016
```

<210> SEQ ID NO 6
<211> LENGTH: 671
<212> TYPE: PRT
<213> ORGANISM: Homo sapiens

<400> SEQUENCE: 6

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg Arg Arg Ala Leu His Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
```

```
                    260                 265                 270
Lys Asp Gly Val Pro Leu Pro Leu Pro Pro Ser Pro Val Leu Ile Leu
                275                 280                 285

Pro Glu Ile Gly Pro Gln Asp Gln Gly Thr Tyr Ser Cys Val Ala Thr
            290                 295                 300

His Ser Ser His Gly Pro Gln Glu Ser Arg Ala Val Ser Ile Ser Ile
305                 310                 315                 320

Ile Glu Pro Gly Glu Gly Pro Thr Ala Gly Ser Val Gly Gly Ser
                325                 330                 335

Gly Leu Gly Thr Leu Ala Leu Ala Ala Ser Thr Lys Gly Pro Ser Val
            340                 345                 350

Phe Pro Leu Ala Pro Cys Ser Arg Ser Thr Ser Glu Ser Thr Ala Ala
                355                 360                 365

Leu Gly Cys Leu Val Lys Asp Tyr Phe Pro Glu Pro Val Thr Val Ser
            370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Lys Thr Tyr Thr Cys Asn Val Asp His Lys
            420                 425                 430

Pro Ser Asn Thr Lys Val Asp Lys Arg Val Glu Ser Lys Tyr Gly Pro
                435                 440                 445

Pro Cys Pro Ser Cys Pro Ala Pro Glu Phe Leu Gly Gly Pro Ser Val
        450                 455                 460

Phe Leu Phe Pro Pro Lys Pro Lys Asp Thr Leu Met Ile Ser Arg Thr
465                 470                 475                 480

Pro Glu Val Thr Cys Val Val Asp Val Ser Gln Glu Asp Pro Glu
                485                 490                 495

Val Gln Phe Asn Trp Tyr Val Asp Gly Val Glu Val His Asn Ala Lys
            500                 505                 510

Thr Lys Pro Arg Glu Glu Gln Phe Asn Ser Thr Tyr Arg Val Val Ser
        515                 520                 525

Val Leu Thr Val Leu His Gln Asp Trp Leu Asn Gly Lys Glu Tyr Lys
            530                 535                 540

Cys Lys Val Ser Asn Lys Gly Leu Pro Ser Ser Ile Glu Lys Thr Ile
545                 550                 555                 560

Ser Lys Ala Lys Gly Gln Pro Arg Glu Pro Gln Val Tyr Thr Leu Pro
                565                 570                 575

Pro Ser Gln Glu Glu Met Thr Lys Asn Gln Val Ser Leu Thr Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Arg Leu Thr Val Asp Lys Ser Arg
625                 630                 635                 640

Trp Gln Glu Gly Asn Val Phe Ser Cys Ser Val Met His Glu Ala Leu
                645                 650                 655

His Asn His Tyr Thr Gln Lys Ser Leu Ser Leu Ser Leu Gly Lys
            660                 665                 670

<210> SEQ ID NO 7
<211> LENGTH: 2037
```

<212> TYPE: DNA
<213> ORGANISM: Homo sapiens

<400> SEQUENCE: 7

| | | | | | |
|---|---|---|---|---|---|
| atggcagccg | aacagcagt | tggagcctgg | gtgctggtcc | tcagtctgtg | gggggcagta | 60 |
| gtaggtgctc | aaaacatcac | agcccggatt | ggcgagccac | tggtgctgaa | gtgtaagggg | 120 |
| gcccccaaga | aaccacccca | gcggctggaa | tggaaactga | acacaggccg | acagaagct | 180 |
| tggaaggtcc | tgtctcccca | gggaggaggc | cctgggaca | gtgtggctcg | tgtccttccc | 240 |
| aacggctccc | tcttccttcc | ggctgtcggg | atccaggatg | aggggatttt | ccggtgccag | 300 |
| gcaatgaaca | ggaatggaaa | ggagaccaag | tccaactacc | gagtccgtgt | ctaccagatt | 360 |
| cctgggaagc | cagaaattgt | agattctgcc | tctgaactca | cggctggtgt | tcccaataag | 420 |
| gtggggacat | gtgtgtcaga | gggaagctac | cctgcaggga | ctcttagctg | gcacttggat | 480 |
| gggaagcccc | tggtgccgaa | tgagaaggga | gtatctgtga | aggaacagac | caggagacac | 540 |
| cctgagacag | ggctcttcac | actgcagtcg | gagctaatgg | tgaccccagc | ccggggagga | 600 |
| gatccccgtc | ccaccttctc | ctgtagcttc | agcccaggcc | ttccccgacg | ccgggccttg | 660 |
| cacacagccc | ccatccagcc | ccgtgtctgg | gagcctgtgc | ctctggagga | ggtccaattg | 720 |
| gtggtggagc | cagaaggtgg | agcagtagct | cctggtggaa | ccgtaaccct | gacctgtgaa | 780 |
| gtccctgccc | agccctctcc | tcaaatccac | tggatgaagg | atggtgtgcc | cttgccctt | 840 |
| cccccagcc | ctgtgctgat | cctccctgag | atagggcctc | aggaccaggg | aacctacagc | 900 |
| tgtgtggcca | cccattccag | ccacgggccc | caggaaagcc | gtgctgtcag | catcagcatc | 960 |
| atcgaaccag | gcgaggaggg | gccaactgca | ggctctgtgg | gaggatcagg | gctgggaact | 1020 |
| ctagccctgg | ccgtagcgg | ctccggaagt | ggggcttcca | ccaagggccc | atccgtcttc | 1080 |
| cccctggcgc | cctgctccag | gagcacctcc | gagagcacag | ccgccctggg | ctgcctggtc | 1140 |
| aaggactact | ccccgaacc | ggtgacggtg | tcgtggaact | caggcgccct | gaccagcggc | 1200 |
| gtgcacacct | tcccggctgt | cctacagtcc | tcaggactct | actccctcag | cagcgtggtg | 1260 |
| accgtgccct | ccagcagctt | gggcacgaag | acctacacct | gcaacgtaga | tcacaagccc | 1320 |
| agcaacacca | aggtggacaa | gagagttgag | tccaaatatg | gtccccatg | ccatcatgc | 1380 |
| ccagcacctg | agttcctggg | gggaccatca | gtcttcctgt | tccccccaaa | acccaaggac | 1440 |
| actctcatga | tctcccggac | ccctgaggtc | acgtgcgtgg | tggtggacgt | gagccaggaa | 1500 |
| gaccccgagg | tccagttcaa | ctggtacgtg | gatggcgtgg | aggtgcataa | tgccaagaca | 1560 |
| aagccgcggg | aggagcagtt | caacagcacg | taccgtgtgg | tcagcgtcct | caccgtcctg | 1620 |
| caccaggact | ggctgaacgg | caaggagtac | aagtgcaagg | tctccaacaa | aggcctcccg | 1680 |
| tcctccatcg | agaaaaccat | ctccaaagcc | aaagggcagc | cccgagagcc | acaggtgtac | 1740 |
| accctgcccc | catcccagga | ggagatgacc | aagaaccagg | tcagcctgac | ctgcctggtc | 1800 |
| aaaggcttct | accccagcga | catcgccgtg | gagtgggaga | gcaatgggca | gccggagaac | 1860 |
| aactacaaga | ccacgcctcc | cgtgctggac | tccgacggct | ccttcttcct | ctacagcagg | 1920 |
| ctaaccgtgg | acaagagcag | gtggcaggag | gggaatgtct | tctcatgctc | cgtgatgcat | 1980 |
| gaggctctgc | acaaccacta | cacacagaag | agcctctccc | tgtctctcgg | gaaatga | 2037 |

<210> SEQ ID NO 8
<211> LENGTH: 678
<212> TYPE: PRT
<213> ORGANISM: Homo sapiens

<400> SEQUENCE: 8

-continued

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
        50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg Arg Arg Ala Leu His Thr Ala Pro
210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
290                 295                 300

His Ser Ser His Gly Pro Gln Glu Ser Arg Ala Val Ser Ile Ser Ile
305                 310                 315                 320

Ile Glu Pro Gly Glu Gly Pro Thr Ala Gly Ser Val Gly Gly Ser
                325                 330                 335

Gly Leu Gly Thr Leu Ala Leu Ala Gly Ser Gly Ser Gly Ser Gly Ala
            340                 345                 350

Ser Thr Lys Gly Pro Ser Val Phe Pro Leu Ala Pro Cys Ser Arg Ser
        355                 360                 365

Thr Ser Glu Ser Thr Ala Ala Leu Gly Cys Leu Val Lys Asp Tyr Phe
    370                 375                 380

Pro Glu Pro Val Thr Val Ser Trp Asn Ser Gly Ala Leu Thr Ser Gly
385                 390                 395                 400

Val His Thr Phe Pro Ala Val Leu Gln Ser Ser Gly Leu Tyr Ser Leu
                405                 410                 415

Ser Ser Val Val Thr Val Pro Ser Ser Ser Leu Gly Thr Lys Thr Tyr
```

```
                        420                 425                 430
Thr Cys Asn Val Asp His Lys Pro Ser Asn Thr Lys Val Asp Lys Arg
                    435                 440                 445
Val Glu Ser Lys Tyr Gly Pro Pro Cys Pro Ser Cys Pro Ala Pro Glu
                450                 455                 460
Phe Leu Gly Gly Pro Ser Val Phe Leu Phe Pro Pro Lys Pro Lys Asp
465                 470                 475                 480
Thr Leu Met Ile Ser Arg Thr Pro Glu Val Thr Cys Val Val Val Asp
                485                 490                 495
Val Ser Gln Glu Asp Pro Glu Val Gln Phe Asn Trp Tyr Val Asp Gly
                500                 505                 510
Val Glu Val His Asn Ala Lys Thr Lys Pro Arg Glu Glu Gln Phe Asn
                515                 520                 525
Ser Thr Tyr Arg Val Val Ser Val Leu Thr Val Leu His Gln Asp Trp
                530                 535                 540
Leu Asn Gly Lys Glu Tyr Lys Cys Lys Val Ser Asn Lys Gly Leu Pro
545                 550                 555                 560
Ser Ser Ile Glu Lys Thr Ile Ser Lys Ala Lys Gly Gln Pro Arg Glu
                565                 570                 575
Pro Gln Val Tyr Thr Leu Pro Pro Ser Gln Glu Glu Met Thr Lys Asn
                580                 585                 590
Gln Val Ser Leu Thr Cys Leu Val Lys Gly Phe Tyr Pro Ser Asp Ile
                595                 600                 605
Ala Val Glu Trp Glu Ser Asn Gly Gln Pro Glu Asn Asn Tyr Lys Thr
                610                 615                 620
Thr Pro Pro Val Leu Asp Ser Asp Gly Ser Phe Phe Leu Tyr Ser Arg
625                 630                 635                 640
Leu Thr Val Asp Lys Ser Arg Trp Gln Glu Gly Asn Val Phe Ser Cys
                645                 650                 655
Ser Val Met His Glu Ala Leu His Asn His Tyr Thr Gln Lys Ser Leu
                660                 665                 670
Ser Leu Ser Leu Gly Lys
            675

<210> SEQ ID NO 9
<211> LENGTH: 10
<212> TYPE: PRT
<213> ORGANISM: Artificial
<220> FEATURE:
<223> OTHER INFORMATION: synthetic peptide

<400> SEQUENCE: 9

Glu Gln Lys Leu Ile Ser Glu Glu Asp Leu
1               5                   10

<210> SEQ ID NO 10
<211> LENGTH: 9
<212> TYPE: PRT
<213> ORGANISM: Artificial
<220> FEATURE:
<223> OTHER INFORMATION: synthetic peptide

<400> SEQUENCE: 10

Tyr Pro Tyr Asp Val Pro Asp Tyr Ala
1               5

<210> SEQ ID NO 11
<211> LENGTH: 575
<212> TYPE: PRT
```

<213> ORGANISM: Mus musculus

<400> SEQUENCE: 11

```
Met Pro Ala Gly Thr Ala Ala Arg Ala Trp Val Leu Val Leu Ala Leu
1               5                   10                  15

Trp Gly Ala Val Ala Gly Gly Gln Asn Ile Thr Ala Arg Ile Gly Glu
            20                  25                  30

Pro Leu Val Leu Ser Cys Lys Gly Ala Pro Lys Lys Pro Pro Gln Gln
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Ile Leu Pro Asn
65                  70                  75                  80

Gly Ser Leu Leu Leu Pro Ala Thr Gly Ile Val Asp Glu Gly Thr Phe
                85                  90                  95

Arg Cys Arg Ala Thr Asn Arg Arg Gly Lys Glu Val Lys Ser Asn Tyr
            100                 105                 110

Arg Val Arg Val Tyr Gln Ile Pro Gly Lys Pro Glu Ile Val Asp Pro
        115                 120                 125

Ala Ser Glu Leu Thr Ala Ser Val Pro Asn Lys Val Gly Thr Cys Val
    130                 135                 140

Ser Glu Gly Ser Tyr Pro Ala Gly Thr Leu Ser Trp His Leu Asp Gly
145                 150                 155                 160

Lys Leu Leu Ile Pro Asp Gly Lys Glu Thr Leu Val Lys Glu Glu Thr
                165                 170                 175

Arg Arg His Pro Glu Thr Gly Leu Phe Thr Leu Arg Ser Glu Leu Thr
            180                 185                 190

Val Ile Pro Thr Gln Gly Gly Thr His Pro Thr Phe Ser Cys Ser Phe
        195                 200                 205

Ser Leu Gly Leu Pro Arg Arg Arg Pro Leu Asn Thr Ala Pro Ile Gln
    210                 215                 220

Leu Arg Val Arg Glu Pro Gly Pro Glu Gly Ile Gln Leu Leu Val
225                 230                 235                 240

Glu Pro Glu Gly Gly Ile Val Ala Pro Gly Gly Thr Val Thr Leu Thr
                245                 250                 255

Cys Ala Ile Ser Ala Gln Pro Pro Gln Val His Trp Ile Lys Asp
            260                 265                 270

Gly Ala Pro Leu Pro Leu Ala Pro Ser Pro Val Leu Leu Leu Pro Glu
        275                 280                 285

Val Gly His Glu Asp Glu Gly Thr Tyr Ser Cys Val Ala Thr His Pro
    290                 295                 300

Ser His Gly Pro Gln Glu Ser Pro Pro Val Ser Ile Arg Val Thr Glu
305                 310                 315                 320

Thr Gly Asp Glu Gly Pro Ala Glu Gly Ser Val Gly Glu Ser Gly Leu
                325                 330                 335

Gly Thr Leu Ala Leu Ala Glu Pro Arg Gly Pro Thr Ile Lys Pro Cys
            340                 345                 350

Pro Pro Cys Lys Cys Pro Ala Pro Asn Leu Leu Gly Gly Pro Ser Val
        355                 360                 365

Phe Ile Phe Pro Pro Lys Ile Lys Asp Val Leu Met Ile Ser Leu Ser
    370                 375                 380

Pro Ile Val Thr Cys Val Val Val Asp Val Ser Glu Asp Asp Pro Asp
385                 390                 395                 400

Val Gln Ile Ser Trp Phe Val Asn Asn Val Glu Val His Thr Ala Gln
```

|   |   |   |   |   | 405 |   |   |   |   | 410 |   |   |   |   | 415 |   |
|---|---|---|---|---|---|---|---|---|---|---|---|---|---|---|---|---|
| Thr | Gln | Thr | His | Arg | Glu | Asp | Tyr | Asn | Ser | Thr | Leu | Arg | Val | Val | Ser |   |
|   |   |   | 420 |   |   |   |   | 425 |   |   |   |   | 430 |   |   |   |
| Ala | Leu | Pro | Ile | Gln | His | Gln | Asp | Trp | Met | Ser | Gly | Lys | Glu | Phe | Lys |   |
|   |   | 435 |   |   |   |   | 440 |   |   |   |   | 445 |   |   |   |   |
| Cys | Lys | Val | Asn | Asn | Lys | Asp | Leu | Pro | Ala | Pro | Ile | Glu | Arg | Thr | Ile |   |
|   | 450 |   |   |   |   | 455 |   |   |   |   | 460 |   |   |   |   |   |
| Ser | Lys | Pro | Lys | Gly | Ser | Val | Arg | Ala | Pro | Gln | Val | Tyr | Val | Leu | Pro |   |
| 465 |   |   |   |   | 470 |   |   |   |   | 475 |   |   |   |   | 480 |   |
| Pro | Pro | Glu | Glu | Glu | Met | Thr | Lys | Lys | Gln | Val | Thr | Leu | Thr | Cys | Met |   |
|   |   |   |   | 485 |   |   |   |   | 490 |   |   |   |   | 495 |   |   |
| Val | Thr | Asp | Phe | Met | Pro | Glu | Asp | Ile | Tyr | Val | Glu | Trp | Thr | Asn | Asn |   |
|   |   |   | 500 |   |   |   |   | 505 |   |   |   |   | 510 |   |   |   |
| Gly | Lys | Thr | Glu | Leu | Asn | Tyr | Lys | Asn | Thr | Glu | Pro | Val | Leu | Asp | Ser |   |
|   |   | 515 |   |   |   |   | 520 |   |   |   |   | 525 |   |   |   |   |
| Asp | Gly | Ser | Tyr | Phe | Met | Tyr | Ser | Lys | Leu | Arg | Val | Glu | Lys | Lys | Asn |   |
|   | 530 |   |   |   |   | 535 |   |   |   |   | 540 |   |   |   |   |   |
| Trp | Val | Glu | Arg | Asn | Ser | Tyr | Ser | Cys | Ser | Val | Val | His | Glu | Gly | Leu |   |
| 545 |   |   |   |   | 550 |   |   |   |   | 555 |   |   |   |   | 560 |   |
| His | Asn | His | His | Thr | Thr | Lys | Ser | Phe | Ser | Arg | Thr | Pro | Gly | Lys |   |   |
|   |   |   |   | 565 |   |   |   | 570 |   |   |   |   |   | 575 |   |   |

RAGE FUSION PROTEINS

RELATED APPLICATIONS

A This application is a national stage application (under 35 U.S.C. 371) of PCT/US2008/066956, filed Jun. 13, 2008, which claims benefit of U.S. Provisional Application 60/943,994, filed Jun. 14, 2007, the entire contents of which are specifically incorporated herein by reference.

FIELD OF THE INVENTION

The present invention relates generally to advanced glycation end products ("AGE") and more specifically to certain fusion proteins that comprise the receptor for advanced glycation end products ("RAGE"). Fusion proteins of the invention bind to AGE and other RAGE ligands (e.g., S100 and HMGB1) and compositions comprising fusion proteins of the invention may be used for the treatment of diseases.

BACKGROUND

Advanced glycation end products (AGE) are the result of nonenzymatic glycation and oxidation of proteins. They appear under stress related circumstances including in autoimmune connective tissue diseases, and may form in inflamed tissue due to the oxidation or the myeloperoxidase pathway AGE have been implicated in a number of diabetes related complications. For example, the characteristic structural changes of diabetic nephropathy, thickened glomerular basement membrane and mesangial expansion, are accompanied by accumulation of AGE, leading to glomerulosclerosis and interstitial fibrosis. Prolonged infusion of nondiabetic rats with AGE has led to the development of similar morphological changes and significant proteinuria. AGE inhibitors such as aminoguanidine have been shown to prevent diabetic nephropahty in diabetic animal models and were recently shown to do the same in one clinical trial on diabetic patients. Also, AGE are a well validated therapeutic target for diabetic retinopathy. Extensive diabetic murine and rat studies have demonstrated the benefit of inhibiting AGE formation in treating this disease.

Atherosclerosis is significantly accelerated in diabetic patients and is associated with greater risk of cardiovascular and cerebrovascular mortality. Animal and human studies have suggested that AGE play a significant role in the formation and progression of atherosclerotic lesions. Increased AGE accumulation in the diabetic vascular tissues has been associated with changes in endothelial cell, macrophage, and smooth muscle cell function.

AGE interact with cell surface receptors on monocytes, macrophages, endothelial cells of the microvasculature, smooth muscle cells, mesengial cells, and neurons. The receptor for advanced glycation end products (RAGE) is a member of the immunoglobulin superfamily of cell surface receptors. RAGE is made up of three extracellular immunoglobulin-like domains, a transmembrane domain, and a cytoplasmic domain that is involved in signaling. RAGE binds multiple ligands in addition to AGE including S100/calgranulins, amphoterin/HMGB1, and amyloid fibrils. RAGE acts through a signal cascade involving NF-kB. RAGE expression is up-regulated in the presence of RAGE ligands and is elevated in joints of subjects with rheumatoid arthritis (RA).

RAGE has a secreted isoform lacking a transmembrane domain called soluble RAGE (sRAGE). Administration of sRAGE has been shown to restore wound healing (Goova, et al. (2001) *Am. J. Pathol.* 159, 513-525) and suppress diabetic atherosclerosis (Park, et al. (1998) *Nat Med.* 4(9):1025-31). Fusion proteins consisting of a RAGE ligand binding element and an immunoglobulin element are discussed in WO 2004/016229 A2 (Wyeth, Madison, N.J.) and US Patent App. Publication 2006/10057679 A1 (O'Keefe, T. et al.).

There exists a need for novel methods of treatment of AGE-mediated diseases, such as diseases that are associated with an elevated amount of AGE. This need and others are met by the present invention.

SUMMARY OF THE INVENTION

The present invention provides materials and methods for the treatment of diseases associated with an elevated amount of AGE. In one embodiment, the present invention provides a fusion protein comprising at least one polypeptide comprising: (a) a first amino acid sequence at least 95% identical to a mammalian receptor for advanced glycation end product (RAGE) ligand binding domain, the first amino acid sequence capable of binding a RAGE ligand; and (b) as second amino acid sequence at least 95% identical to a human heavy chain immunoglobulin IgG4 constant domain or a fragment thereof; wherein the first amino acid sequence comprises at least one mutation relative to a wild type RAGE ligand binding domain. In one embodiment of the invention, a fusion protein of the invention may further comprise a linker sequence between the first amino acid sequence and the second ammo acid sequence. In some embodiments, the RAGE ligand binding domain may be from a mammalian RAGE, for example, a human RAGE. A suitable mammalian RAGE ligand binding domain may comprise amino acids 1-344 of SEQ ID NO: 6 or amino acids 24-344 of SEQ ID NO: 6. In one embodiment, a fusion protein of the invention may comprise an amino acid sequence selected from the group consisting of SEQ ID NO: 2, SEQ ID NO:4, SEQ ID NO:6, and SEQ ID NO:8. In one embodiment, an isolated fusion protein of the invention comprises SEQ ID NO:6 or SEQ ID NO:8. In another embodiment, an isolated fusion protein of the invention consists of SEQ ID NO:6 or SEQ ID NO:8. In some embodiments of the invention, fusion proteins of the invention may further comprise a linker between the RAGE amino acid sequence and the IgG4 amino acid sequence. The present invention also contemplates nucleic acid molecules (e.g., DNA or RNA molecules) encoding the fusion proteins of the invention as well as host cells expressing the nucleic acid molecules encoding the fusion proteins of the invention.

The present invention further provides for a pharmaceutical composition comprising a fusion protein of the invention and a pharmaceutically acceptable excipient or diluent.

The present invention provides methods of treating diseases mediated by AGE. Such diseases include any disease characterized by an increased amount of AGE in a subject, for example, a mammal such as a human. Methods of treating an AGE-mediated disease comprise administering to a subject having an AGE-mediated disease a therapeutically effective amount of a pharmaceutical composition comprising a fusion protein of the invention. Examples of diseases that can be treated by the methods of the invention include, but are not limited to, diabetic nephropathy, rheumatoid arthritis, and autoimmune diseases such as dermatitis, glomerulonephritis, multiple sclerosis, uveitis ophthalmia, autoimmune pulmonary inflammation, insulin dependent diabetes mellitus, autoimmune inflammatory eye, systemic lupus erythematosus, insulin resistance, rheumatoid arthritis, diabetic retinopathy, and scleroderma. Any fusion protein of the invention may be used in the practice of the methods of the invention. In one embodiment, methods of the invention may be practiced using a fusion protein comprising SEQ ID NO:6 or SEQ ID NO:8. In another embodiment, methods of the invention may be practiced using a fusion protein that consists of SEQ ID NO:6 or SEQ ID NO:8.

In another embodiment of the invention, the present invention provides methods of lowering the levels of ligand bound by RAGE in a mammal (e.g., a human) in need thereof. Such methods may comprise administering to the mammal a RAGE ligand-lowering amount of a fusion protein of the invention.

In other embodiments, the invention provides for a recombinant expression vector comprising the DNA sequences of the invention; a host cell transformed, transduced, or transfected with the vector; and a process for producing a fusion protein, which comprises culturing a host cell transformed, transduced or transfected with a nucleic acid encoding a fusion protein of the invention under conditions suitable to effect expression of the fusion protein.

The invention further provides compositions comprising the present fusion protein or fragments thereof. In some embodiments, the invention includes compositions comprising the present fusion protein or fragments thereof to which a radioisotope, chelator, toxin, fluorochrome, biotin, peptide epitopes such as his-tags, myc-tags, or sugars are directly or indirectly attached. Other embodiments of the invention include the present fusion protein fused with another protein for the purposes of altering the biological half-life or function and glycosylation variants of the fusion protein.

These and other aspects of the present invention will become evident upon reference to the following detailed description.

DETAILED DESCRIPTION OF THE INVENTION

Definitions

Figure 1:
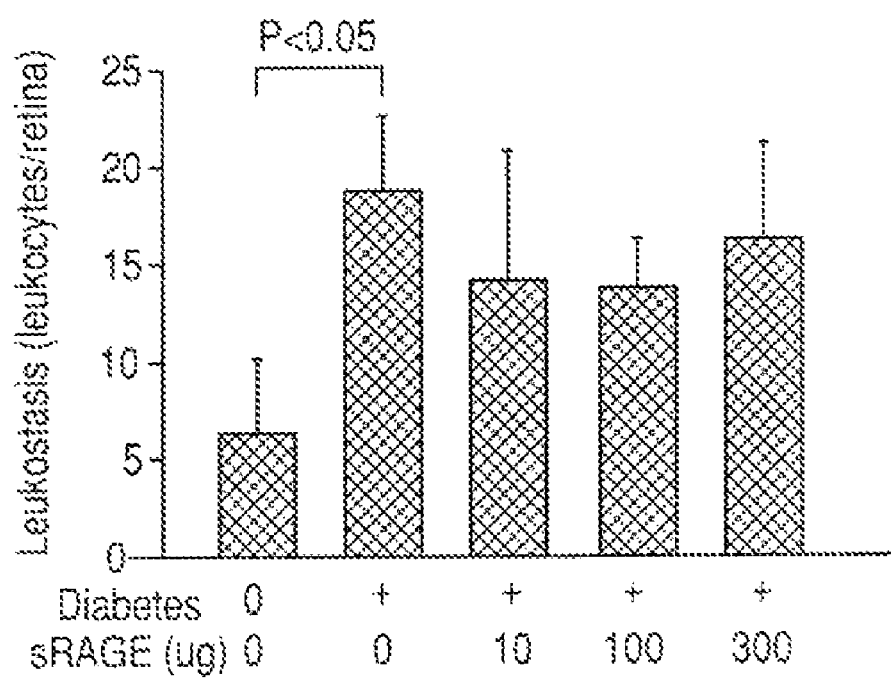
FIG. 1 is a bar graph showing the effects of an exemplary RAGE-Ig fusion protein on leukostasis in a streptozotocin-induced diabetic mouse model.
Figure 2A:
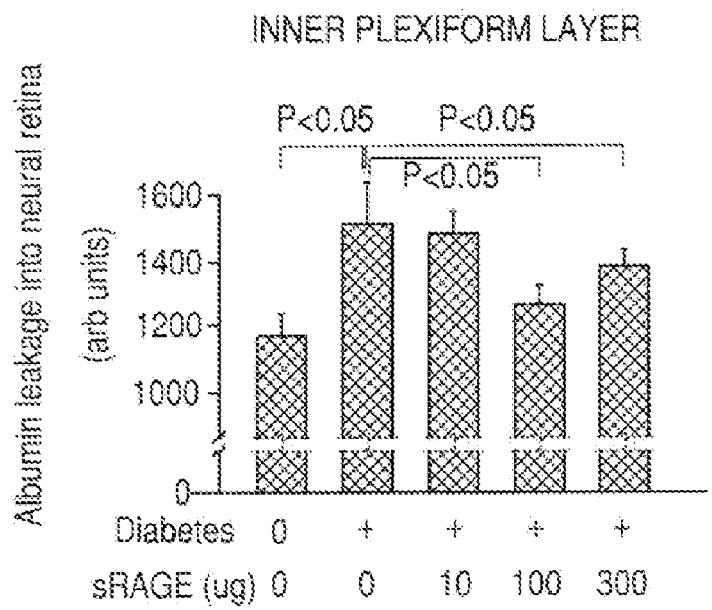
FIG. 2A-AD are bar graphs showing the effects of an exemplary RAGE-Ig fusion protein on retinal vascular permeability in various retinal layers in a streptozotocin-induced diabetic mouse model.
Figure 2B:
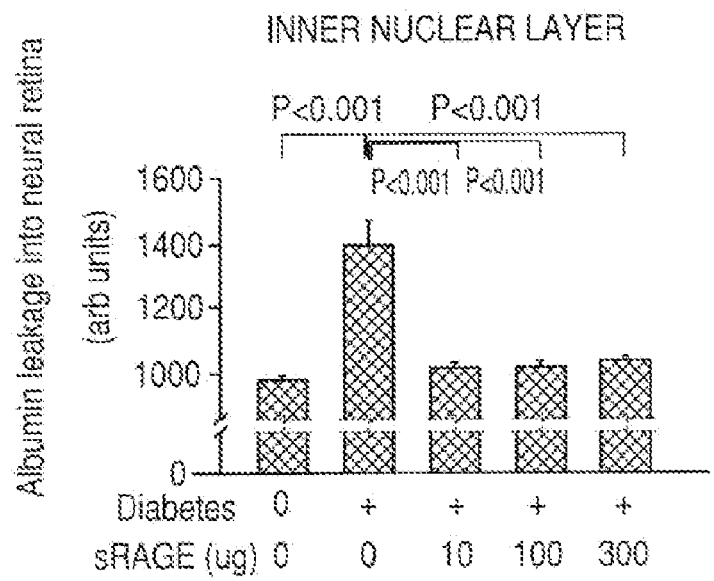
Figure 2C:
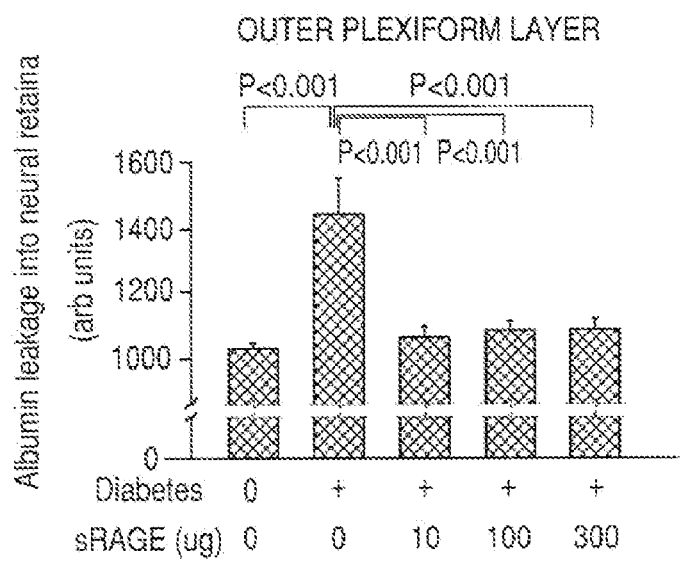
Figure 2D:
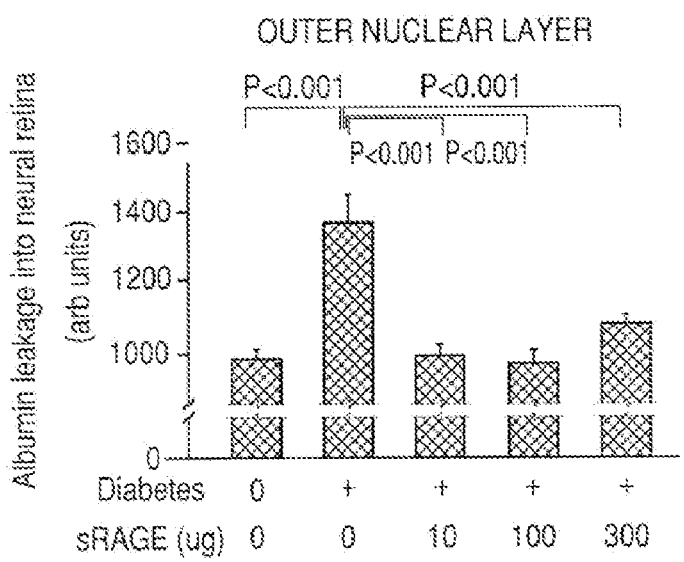

As used herein the terms "receptor for advanced glycation end product" or RAGE refer to proteins having amino acid sequences that are substantially similar to the native mammalian RAGE amino acid sequences and function to bind one or more RAGE ligands in a ligand-receptor specific manner. The terms "advanced glycation end product" and "AGE" refer to a heterogeneous group of molecules formed from the nonenzymatic reaction of reducing sugars with free amino groups of proteins, lipids, and nucleic acids as described above.

As used herein, a "RAGE ligand binding domain" or "RAGE-LBD" refers to any mammalian RAGE protein or any portion of a mammalian RAGE protein that retains the ability to bind a RAGE ligand in a ligand-receptor specific manner. Specifically, without limitation, a RAGE ligand binding domain includes a polypeptide having one or more extracellular domains of a transmembrane RAGE protein. With reference to Table 6, a suitable RAGE-LBD may comprise at least amino acids 1-99, or amino acids 24-99, or amino acids 1-208, or amino acids 24-208, or amino acids 1-301, or amino acids 24-301, or amino acids 1-344, or amino acids 24-344 of SEQ ID NO:6.

The term "isolated," as used in the context of this specification to define the purity of the fusion protein, means that the protein is substantially free of other proteins with which it is associated during production, including without limitation substantially free of other proteins present during expression of the fusion protein in a cell culture medium. For example, an isolated protein of the invention may comprise 1-25%, 20-25%, 15-20%, 10-15%, 5-10%, 1-5% or less than about 2% by mass of protein contaminants residual of production processes. Compositions comprising isolated proteins of the invention, however, can contain other proteins added as stabilizers, carriers, excipients or co-therapeutics.

As used herein, "protein" and "polypeptide" are interchangeable.

As used herein "treating" a disease or disorder refers to improving at least one sign or symptom of the subject's disease or disorder.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "or" is used herein to mean, and is used interchangeably with, the term "and/or," unless context clearly indicates otherwise.

The term "percent identical" refers to sequence identity between two amino acid sequences or between two nucleotide sequences. Percent identity can be determined by comparing a position in each sequence which may be aligned for purposes of comparison. Expression as a percentage of identity refers to a function of the number of identical amino acids or nucleic acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Sequence identity may be determined by comparing a reference sequence or a subsequence of the reference sequence to a test sequence (e.g., a nucleotide sequence, an amino acid sequence, etc.). The reference sequence and the test sequence are optimally aligned over an arbitrary number of residues termed a comparison window. In order to obtain optimal alignment, additions or deletions, such as gaps, may be introduced into the test sequence. The percent sequence identity is determined by determining the number of positions at which the same residue is present in both sequences and dividing the number of matching positions by the total length of the sequences in the comparison window and multiplying by 100 to give the percentage. In addition to the number of matching positions, the number and size of gaps is also considered in calculating the percentage sequence identity.

Sequence identity is typically determined using computer programs. A representative program is the BLAST (Basic Local Alignment Search Tool) program publicly accessible at the National Center for Biotechnology Information (NCBI http://www.ncbi.nlm.nih.gov/). This program compares segments in a test sequence to sequences in a database to determine the statistical significance of the matches, then identifies and reports only those matches that are more significant than a threshold level. A suitable version of the BLAST program is one that allows gaps, for example, version 2.X (Altschul, et al., Nucleic Acids Res 25(17):3389-402, 1997). Additional suitable programs for identifying proteins with sequence identity to the proteins of the invention include, but are not limited to, PHI-BLAST (Pattern Hit Initiated BLAST, Zhang, et al., Nucleic Acids Res 26(17):3986-90, 1998) and PSI-BLAST (Position-Specific iterated BLAST. Altschul, et al., Nucleic Acids Res 25(17):3389-402, 1997). The programs are publicly available at the NCBI web site listed above and may be used with the default settings in order to determine sequence identity according to the invention.

Fusion Proteins

The present invention provides an isolated fusion protein comprising at least one polypeptide comprising: (a) a first amino acid sequence at least 90%, 91%, 92%, 93%, 94%, 95%, 96%, 97%, 98%, or 99% identical to a mammalian receptor for advanced glycation end product (RAGE) ligand binding domain, the first amino acid sequence capable of binding a RAGE ligand; and (b) a second amino acid sequence at least 90%, 91%, 92%, 93%, 94%, 95%, 96%, 97%, 98%, or 99% identical to a human heavy chain immunoglobulin IgG4 constant domain or a fragment thereof, wherein the first amino acid sequence comprises at least one mutation, or at least two mutations, or at least three mutations, or 1-4 mutations, or 1-10 mutations relative to a wild type RAGE ligand binding domain. Examples of mutations that may be made in the first amino acid sequence are those that increase the stability of the fusion protein, for example, by making the RAGE ligand binding domain more resistant to proteolytic degradation, such as those that make the fusion protein more resistant to furin-like proteases. Suitable fragments of the second amino acid sequence include fragments that retain the ability to increase the serum half-life of the fusion proteins of which they are part relative to the serum half life of the same first amino acid sequence alone. Preferably the first amino acid sequence and the second amino acid sequence are derived from human RAGE ligand binding domain and human IgG4.

Fusion proteins of the invention may comprise one or more amino acid sequences in addition to a RAGE ligand binding domain and an IgG4 constant domain or fragment thereof. For example, a fusion protein of the invention may comprise a linker sequence which may be inserted between the RAGE ligand binding domain and the IgG sequence. Fusion proteins of the invention may comprise one or more tag sequences, for example, purification tag sequences such as 6-Histidines. Fusion proteins of the invention may comprise one or more epitopes recognized by commercially available antibodies, for example, c-myc (EQKLISEEDI, SEQ ID NO: 9) and hemagglutinin (YPYDVPDYA, SEQ ID NO:10) derived from an epitope tag of the influenza hemagglutinin protein.

Any mammalian RAGE protein known to those of skill in the art may be used in the practice of the present invention. Preferably the extracellular domain of the RAGE protein will be used to identify a ligand binding domain that can be mutated and used as the first amino acid sequence of the fusion protein. Suitable example of mammalian RAGE proteins include, but are not limited to, primate, human (e.g., (GenBank accession no. NP_001127 and NP_751947), murine (e.g., GenBank accession no. NP_31451), canine (e.g., GenBank accession no AAQ81297), rat (e.g., GenBank accession no. NP_445788), feline, bovine (e.g., GenBank accession no. AAI20128), ovine, equine and porcine (e.g., GenBank accession no. AAQ73283) RAGE domains.

RAGE amino acid sequences comprising one or more changes or modifications with respect to the wild type sequence may be used in the present invention. Such changes or modifications include, but are not limited to, point mutations, deletions from the N-terminal, deletions from the C-terminal, internal deletions, and combinations thereof. Any change or modification may be introduced into a RAGE sequence for use in the present invention so long as the resulting protein retains biological activity, e.g., the ability to bind one or more RAGE ligands. The fusion proteins of the invention also include those with or without endogenous glycosylation patterns, including without limitation, fusion proteins in which the first amino acid sequence is derived from a mammalian RAGE ligand binding domain with or without associated native-pattern glycosylation of the binding domain.

Any suitable IgG Fc region may be used in the practice of the invention, preferably, from an IgG4 molecule, for example, amino acid residues 149-473 of GenBank accession no. AAH-25985. An IgG region for use in the present invention may be an IgG4 Fc region and may comprise one or more of the CH2 and CH3 regions of the IgG4 molecule.

Examples of suitable fusion proteins are provided in the following tables.

Table 1 provides the nucleotide sequence of a human RAGE-IgG4 Fc fusion protein gene sequence.

TABLE 1

Human RAGE-IgG4 Fc Fusion Gene Sequence.

(SEQ. ID NO: 1)
ATGGCAGCCGGAACAGCAGTTGGAGCCTGGGTGCTGGTCCTCAGTCT

GTGGGGGGCAGTAGTAGGTGCTCAAAACATCACAGCCCGGATTGGCG

AGCCACTGGTGCTGAAGTGTAAGGGGCCCCCAAGAAACCACCCCAGC

GGCTGGAATGGAAACTGAACACAGGCCGGACAGAAGCCTGGAAGGTCC

TGTCTCCCCAGGGAGGAGGCCCCTGGGACAGTGTGGCTCGTGTCCTTC

CCAACGGCTCCCTCTTCCTTCCGGCTGTCGGGATCCAGGATGAGGGGA

TTTTCCGGTGCCAGGCAATGAACAGGAATGGAAAGGAGACCAAGTCCA

ACTACCGAGTCCGTGTCTACCAGATTCCTGGGAAGCCAGAAATTGTAG

ATTCTGCCTCTGAACTCACGGCTGGTGTTCCCAATAAGGTGGGGACAT

GTGTGTCAGAGGGAAGCTACCCTGCAGGGACTCTTAGCTGGCACTTGG

ATGGGAAGCCCCTGGTGCCGAATGAGAAGGGAGTATCTGTGAAGGAAC

AGACCAGGAGACACCCTGAGACAGGGCTCTTCACACTGCAGTCGGAGC

TAATGGTGACCCCAGCCCGGGGAGGAGATCCCCGTCCCACCTTCTCCT

GTAGCTTCAGCCCAGGCCTTCCCCGACACCGGGCCTTGCGCACAGCCC

CCATCCAGCCCCGTGTCTGGGAGCCTGTGCCTCTGGAGGAGGTCCAAT

TGGTGGTGGAGCCAGAAGGTGGAGCAGTAGCTCCTGGTGGAACCGTAA

TABLE 1-continued

Human RAGE-IgG4 Fc Fusion Gene Sequence.

CCCTGACCTGTGAAGTCCCTGCCCAGCCCTCTCCTCAAATCCACTGGA

TGAAGGATGGTGTGCCCTTGCCCCTTCCCCCCAGCCCTGTGCTGATCC

TCCCTGAGATAGGGCCTCAGGACCAGGGAACCTACAGCTGTGTGGCCA

CCCATTCCAGCCACGGGCCCCAGGAAAGCCGTGCTGTCAGCATCAGCA

TCATCGAACCAGGCGAGGAGGGGCCAACTGCAGGCTCTGTGGGAGGAT

CAGGGCTGGGAACTCTAGCCCTGGCC<u>GCTTCCACCAAGGGCCCATCCG</u>

<u>TCTTCCCCCTGGCGCCCTGCTCCAGGAGCACCTCCGAGAGCACAGCCG</u>

<u>CCCTGGGCTGCCTGGTCAAGGACTACTTCCCCGAACCGGTGACGGTGT</u>

<u>CGTGGAACTCAGGCGCCCTGACCAGCGGCGTGCACACCTTCCCGGCTG</u>

<u>TCCTACAGTCCTCAGGACTCTACTCCCTCAGCAGCGTGGTGACCGTGC</u>

<u>CCTCCAGCAGCTTGGGCACGAAGACCTACACCTGCAACGTAGATCACA</u>

<u>AGCCCAGCAACACCAAGGTGGACAAGAGAGTTGAGTCCAAATATGGTC</u>

<u>CCCCATGCCCATCATGCCCAGCACCTGAGTTCCTGGGGGGACCATCAG</u>

<u>TCTTCCTGTTCCCCCCAAAACCCAAGGACACTCTCATGATCTCCCGGA</u>

<u>CCCCTGAGGTCACGTGCGTGGTGGTGGACGTGAGCCAGGAAGACCCCG</u>

<u>AGGTCCAGTTCAACTGGTACGTGGATGGCGTGGAGGTGCATAATGCCA</u>

<u>AGACAAAGCCGCGGGAGGAGCAGTTCAACAGCACGTACCGTGTGGTCA</u>

<u>GCGTCCTCACCGTCCTGCACCAGGACTGGCTGAACGGCAAGGAGTACA</u>

<u>AGTGCAAGGTCTCCAACAAAGGCCTCCCGTCCTCCATCGAGAAAACCA</u>

<u>TCTCCAAAGCCAAAGGGCAGCCCCGAGAGCCACAGGTGTACACCCTGC</u>

<u>CCCCATCCCAGGAGGAGATGACCAAGAACCAGGTCAGCCTGACCTGCC</u>

<u>TGGTCAAAGGCTTCTACCCCAGCGACATCGCCGTGGAGTGGGAGAGCA</u>

<u>ATGGGCAGCCGGAGAACAACTACAAGACCACGCCTCCCGTGCTGGACT</u>

<u>CCGACGGCTCCTTCTTCCTCTACAGCAGGCTAACCGTGGACAAGAGCA</u>

<u>GGTGGCAGGAGGGGAATGTCTTCTCATGCTCCGTGATGCATGAGGCTC</u>

<u>TGCACAACCACTACACACAGAAGAGCCTCTCCCTGTCTCTCGGGAAAT</u>

<u>GA</u>

Bold text is the coding sequence for the RAGE signal sequence, normal text is the coding sequence for human RAGE, and underlined text is the coding sequence for IgG4 Fc region.

TABLE 2

Amino acid sequence of a human RAGE-IgF4Fc fusion protein.

(SEQ ID NO: 2)
MAAGTAVGAW VLVLSLWGAV VGAQNITARI GEPLVLKCKG APKKPPQRLE    50

WKLNTGRTEA WKVLSPQGGG PWDSVARVLP NGSLFLPAVG IQDEGIFRCQ    100

AMNRNGKETK SNYRVRVYQI PGKPEIVDSA SELTAGVPNK VGTCVSEGSY    150

PAGTLSWHLD GKPLVPNEKG VSVKEQTRRH PETGLFTLQS ELMVTPARGG    200

DPRPTFSCSF SPGLPRHRAL RTAPIQPRVW EPVPLEEVQL VVEPEGGAVA    250

TABLE 2-continued

Amino acid sequence of a human RAGE-IgF4Fc fusion protein.

| | | | | |
|---|---|---|---|---|
| PGGTVTLTCE | VPAQPSPQIH | WMKDGVPLPL | PPSPVLILPE | IGPQDQGTYS | 300 |
| CVATHSSHGP | QESRAVSISI | IEPGEEGPTA | GSVGGSGLGT | LALAASTKGP | 350 |
| SVFPLAPCSR | STSESTAALG | CLVKDYFPEP | VTVSWNSGAL | TSGVHTFPAV | 400 |
| LQSSGLYSLS | SVVTVPSSSL | GTKTYTCNVD | HKPSNTKVDK | RVESKYGPPC | 450 |
| PSCPAPEFLG | GPSVFLFPPK | PKDTLMISRT | PEVTCVVVDV | SQEDPEVQFN | 500 |
| WYVDGVEVHN | AKTKPREEQF | NSTYRVVSVL | TVLHQDWLNG | KEYHCHVSNK | 550 |
| GLPSSIEKTI | SKAKGQPREP | QVYTLPPSQE | EMTKNQVSLT | CLVKGFYPSD | 600 |
| IAVEWESNGQ | PENNYKTTPP | VLDSDGSFFL | YSRLTVDKSR | WQEGNVFSCS | 650 |
| VMHEALHNHY | TQKSLSLSLG | K | | | |

Bold text is the amino acid sequence for the RAGE signal sequence, normal text is the amino acid sequence for human RAGE, and underlined text is the amino acid sequence for IgG4 Fc region.

TABLE 3

Human RAGE-Linker-IgG4 Fc Fusion Gene Sequence.

(SEQ ID NO: 3)
ATGGCAGCCGGAACAGCAGTTGGAGCCTGGGTGCTGGTCCTCAGTCT
GTGGGGGGCAGTAGTAGGTGCTCAAAACATCACAGCCCGGATTGGCG
AGCCACTGGTGCTGAAGTGTAAGGGGCCCCCAAGAAACCACCCCAG
CGGCTGGAATGGAAACTGAACACAGGCCGGACAGAAGCCTGGAAGGT
CCTGTCTCCCCAGGGAGGAGGCCCCTGGGACAGTGTGGCTCGTGTCC
TTCCCAACGGCTCCCTCTTCCTTCCGGCTGTCGGGATCCAGGATGAG
GGGATTTTCCGGTGCCAGGCAATGAACAGGAATGGAAAGGAGACCAA
GTCCAACTACCGAGTCCGTGTCTACCAGATTCCTGGGAAGCCAGAAA
TTGTAGATTCTGCCTCTGAACTCACGGCTGGTGTTCCCAATAAGGTG
GGGACATGTGTGTCAGAGGGAAGCTACCCTGCAGGGACTCTTAGCTG
GCACTTGGATGGGAAGCCCCTGGTGCCGAATGAGAAGGGAGTATCTG
TGAAGGAACAGACCAGGAGACACCCTGAGACAGGGCTCTTCACACTG
CAGTCGGAGCTAATGGTGACCCCAGCCCGGGGAGGAGATCCCCGTCC
CACCTTCTCCTGTAGCTTCAGCCCAGGCCTTCCCCGACACCGGGCCT
TGCGCACAGCCCCCATCCAGCCCCGTGTCTGGGAGCCTGTGCCTCTG
GAGGAGGTCCAATTGGTGGTGGAGCCAGAAGGTGGAGCAGTAGCTCC
TGGTGGAACCGTAACCCTGACCTGTGAAGTCCCTGCCCAGCCCTCTC
CTCAAATCCACTGGATGAAGGATGGTGTGCCCTTGCCCCTTCCCCCC
AGCCCTGTGCTGATCCTCCCTGAGATAGGGCCTCAGGACCAGGGAAC
CTACAGCTGTGTGGCCACCCATTCCAGCCACGGGCCCCAGGAAAGCC
GTGCTGTCAGCATCAGCATCATCGAACCAGGCGAGGAGGGGCCAACT
GCAGGCTCTGTGGGAGGATCAGGGCTGGGAACTCTAGCCCTGGCCGG
TAGCGGCTCCGGAAGTGGGGCTTCCACCAAGGGCCCATCCGTCTTCC

TABLE 3-continued

Human RAGE-Linker-IgG4 Fc Fusion Gene Sequence.

CCCTGGCGCCCTGCTCCAGGAGCACCTCCGAGAGCACAGCCGCCCTG
GGCTGCCTGGTCAAGGACTACTTCCCCGAACCGGTGACGGTGTCGTG
GAACTCAGGCGCCCTGACCAGCGGCGTGCACACCTTCCCGGCTGTCC
TACAGTCCTCAGGACTCTACTCCCTCAGCAGCGTGGTGACCGTGCCC
TCCAGCAGCTTGGGCACGAAGACCTACACCTGCAACGTAGATCACAA
GCCCAGCAACACCAAGGTGGACAAGAGAGTTGAGTCCAAATATGGTC
CCCCATGCCCATCATGCCCAGCACCTGAGTTCCTGGGGGGACCATCA
GTCTTCCTGTTCCCCCCAAAACCCAAGGACACTCTCATGATCTCCCG
GACCCCTGAGGTCACGTGCGTGGTGGTGGACGTGAGCCAGGAAGACC
CCGAGGTCCAGTTCAACTGGTACGTGGATGGCGTGGAGGTGCATAAT
GCCAAGACAAAGCCGCGGGAGGAGCAGTTCAACAGCACGTACCGTGT
GGTCAGCGTCCTCACCGTCCTGCACCAGGACTGGCTGAACGGCAAGG
AGTACAAGTGCAAGGTCTCCAACAAAGGCCTCCCGTCCTCCATCGAG
AAAACCATCTCCAAAGCCAAAGGGCAGCCCCGAGAGCCACAGGTGTA
CACCCTGCCCCCATCCCAGGAGGAGATGACCAAGAACCAGGTCAGCC
TGACCTGCCTGGTCAAAGGCTTCTACCCCAGCGACATCGCCGTGGAG
TGGGAGAGCAATGGGCAGCCGGAGAACAACTACAAGACCACGCCTCC
CGTGCTGGACTCCGACGGCTCCTTCTTCCTCTACAGCAGGCTAACCG
TGGACAAGAGCAGGTGGCAGGAGGGGAATGTCTTCTCATGCTCCGTG
ATGCATGAGGCTCTGCACAACCACTACACACAGAAGAGCCTCTCCCT
GTCTCTCGGGAAATGA

Bold text is the coding sequence for the RAGE signal sequence, normal text is the coding sequence for human RAGE, double underline text is the coding sequence for the peptide linker, and single underlined text is the coding sequence for IgG4 Fc region.

TABLE 4

Amino acid sequence of a human RAGE-Linker-IgG4Fc fusion protein.

(SEQ ID NO: 4)

| | | | | | |
|---|---|---|---|---|---|
| MAAGTAVGAW | VLVLSIMGAV | VGAQNITARI | GEPLVLKCKG | APKKPPQRLE | 50 |
| WKLNTGRTEA | WKVLSPQGGG | PWDSVARVLP | NGSLFLPAVG | IQDEGIFRCQ | 100 |
| AMNRNGKETK | SNYRVRVYQI | PGKPEIVDSA | SELTAGVPNK | VGTCVSEGSY | 150 |
| PAGTLSWHLD | GKPLVPNEKG | VSVKEQTRRH | PETGLFTLQS | ELMVTPARGG | 200 |
| DPRPTFSCSF | SPGLPRHRAL | RTAPIQPRVW | EPVPLEEVQL | VVEPEGGAVA | 250 |
| PGGTVTLTCE | VPAQPSPQIH | WMKDGVPLPL | PPSPVLILPE | IGPQDQGTYS | 300 |
| CVATHSSHGP | QESRAVSISI | IEPGEEGPTA | GSVGGSGLGT | LALA<u><u>GSGSGS</u></u> | 350 |
| <u><u>GASTKGPSVF</u></u> | <u>PLAPCSRSTS</u> | <u>ESTAALGCLV</u> | <u>KDYFPEPVTV</u> | <u>SWNSGALTSG</u> | 400 |
| <u>VHTFPAVLQS</u> | <u>SGLYSLSSVV</u> | <u>TVPSSSLGTK</u> | <u>TYTCNVDHKP</u> | <u>SNTKVDKRVE</u> | 450 |
| <u>SKYGPPCPSC</u> | <u>PAPEFLGGPS</u> | <u>VFLFPPKPKD</u> | <u>TLMISRTPEV</u> | <u>TCVVVDVSQE</u> | 500 |
| <u>DPEVQFNWYV</u> | <u>DGVEVHNAKT</u> | <u>KPREEQFNST</u> | <u>YRVVSVLTVL</u> | <u>HQDWLNGKEY</u> | 550 |
| <u>KCKVSNKGLP</u> | <u>SSIEKTISKA</u> | <u>KGQPREPQVY</u> | <u>TLPPSQEEMT</u> | <u>KNQVSLTCLV</u> | 600 |
| <u>KGFYPSDIAV</u> | <u>EWESNGQPEN</u> | <u>NYKTTPPVLD</u> | <u>SDGSFFLYSR</u> | <u>LTVDKSRWQE</u> | 650 |
| <u>GNVFSCSVMH</u> | <u>EALHNHYTQK</u> | <u>SLSLSLGK</u> | | | 678 |

Bold text is the amino acid sequence for the RAGE signal sequence, normal text is the amino acid sequence for human RAGE, double underline text is the amino acid sequence for the peptide linker, and single underlined text is the amino acid sequence for IgG4 Fc region.

TABLE 5

Human RAGE variant-IgG4 Fc Fusion Gene Sequence.

(SEQ ID NO: 5)

ATGGCAGCCGGAACAGCAGTTGGAGCCTGGGTGCTGGTCCTCAGTCT

GTGGGGGGCAGTAGTAGGTGCTCAAAACATCACAGCCCGGATTGGCG

AGCCACTGGTGCTGAAGTGTAAGGGGCCCCCAAGAAACCACCCCAG

CGGCTGGAATGGAAACTGAACACAGGCCGGACAGAAGCTTGGAAGGT

CCTGTCTCCCCAGGAGGAGCCCCTGGGACAGTGTGGCTCGTGTCC

TTCCCAACGGCTCCCTCTTCCTTCCGGCTGTCGGGATCCAGGATGAG

GGGATTTTCCGGTGCCAGGCAATGAACAGGAATGGAAAGGAGACCAA

GTCCAACTACCGAGTCCGTGTCTACCAGATTCCTGGGAAGCCAGAAA

TTGTAGATTCTGCCTCTGAACTCACGGCTGGTGTTCCCAATAAGGTG

GGGACATGTGTGTCAGAGGGAAGCTACCCTGCAGGGACTCTTAGCTG

GCACTTGGATGGGAAGCCCCTGGTGCCGAATGAGAAGGGAGTATCTG

TGAAGGAACAGACCAGGAGACACCCTGAGACAGGGCTCTTCACACTG

CAGTCGGAGCTAATGGTGACCCCAGCCCGGGGAGGAGATCCCCGTCC

CACCTTCTCCTGTAGCTTCAGCCCAGGCCTTCCCCGACGCCGGGCCT

TGCACACAGCCCCCATCCAGCCCCGTGTCTGGGAGCCTGTGCCTCTG

GAGGAGGTCCAATTGGTGGTGGAGCCAGAAGGTGGAGCAGTAGCTCC

TGGTGGAACCGTAACCCTGACCTGTGAAGTCCCTGCCCAGCCCTCTC

TABLE 5-continued

Human RAGE variant-IgG4 Fc Fusion Gene Sequence.

CTCAAATCCACTGGATGAAGGATGGTGTGCCCTTGCCCCTTCCCCCC

AGCCCTGTGCTGATCCTCCCTGAGATAGGGCCTCAGGACCAGGGAAC

CTACAGCTGTGTGGCCACCCATTCCAGCCACGGGCCCCAGGAAAGCC

GTGCTGTCAGCATCAGCATCATCGAACCAGGCGAGGAGGGGCCAACT

GCAGGCTCTGTGGGAGGATCAGGGCTGGGAACTCTAGCCCTGGCCGC

<u>TTCCACCAAGGGCCCATCCGTCTTCCCCCTGGCGCCCTGCTCCAGGA</u>

<u>GCACCTCCGAGAGCACAGCCGCCCTGGGCTGCCTGGTCAAGGACTAC</u>

<u>TTCCCCGAACCGGTGACGGTGTCGTGGAACTCAGGCGCCCTGACCAG</u>

<u>CGGCGTGCACACCTTCCCGGCTGTCCTACAGTCCTCAGGACTCTACT</u>

<u>CCCTCAGCAGCGTGGTGACCGTGCCCTCCAGCAGCTTGGGCACGAAG</u>

<u>ACCTACACCTGCAACGTAGATCACAAGCCCAGCAACACCAAGGTGGA</u>

<u>CAAGAGAGTTGAGTCCAAATATGGTCCCCCATGCCCATCATGCCCAG</u>

<u>CACCTGAGTTCCTGGGGGGACCATCAGTCTTCCTGTTCCCCCCAAAA</u>

<u>CCCAAGGACACTCTCATGATCTCCCGGACCCCTGAGGTCACGTGCGT</u>

<u>GGTGGTGGACGTGAGCCAGGAAGACCCCGAGGTCCAGTTCAACTGGT</u>

<u>ACGTGGATGGCGTGGAGGTGCATAATGCCAAGACAAAGCCGCGGGAG</u>

<u>GAGCAGTTCAACAGCACGTACCGTGTGGTCAGCGTCCTCACCGTCCT</u>

<u>GCACCAGGACTGGCTGAACGGCAAGGAGTACAAGTGCAAGGTCTCCA</u>

<u>ACAAAGGCCTCCCGTCCTCCATCGAGAAAACCATCTCCAAAGCCAAA</u>

<u>GGGCAGCCCCGAGAGCCACAGGTGTACACCCTGCCCCCATCCCAGGA</u>

TABLE 5-continued

Human RAGE variant-IgG4 Fc Fusion Gene Sequence.

GGAGATGACCAAGAACCAGGTCAGCCTGACCTGCCTGGTCAAAGGCT

TCTACCCCAGCGACATCGCCGTGGAGTGGGAGAGCAATGGGCAGCCG

GAGAACAACTACAAGACCACGCCTCCCGTGCTGGACTCCGACGGCTC

CTTCTTCCTCTACAGCAGGCTAACCGTGGACAAGAGCAGGTGGCAGG

AGGGGAATGTCTTCTCATGCTCCGTGATGCATGAGGCTCTGCACAAC

CACTACACACAGAAGAGCCTCTCCCTGTCTCTCGGGAAATGA

Bold text is the coding sequence for the RAGE signal sequence, normal text is the coding sequence for human RAGE variant, bold wavy underline letters are sites of the point mutations introduced into the variant hRAGE sequence, and underlined text is the coding sequence for IgG4 Fc region.

TABLE 6

Amino acid sequence of a human RAGE variant-IgG4Fc fusion protein.

(SEQ ID NO: 6)
```
  1  MAAGTAVGAW VLVLSLWGAV VGAQNITARI GEPLVLKCKG APKKPPQRLE
 51  WKLNTGRTEA WKVLSPQGGG PWDSVARVLP NGSLFLPAVG IQDEGIFRCQ
101  AMNRNGKETK SNYRVRVYQI PGKPEIVDSA SELTAGVPNK VGTCVSEGSY
151  PAGTLSWHLD GKPLVPNEKG VSVKEQTRRH PETGLFTLQS ELMVTPARGG
201  DPRPTFSCSP SPGLPRRRAL HTAPIQPRVW EPVPLEEVQL VVEPEGGAVA
251  PGGTVTLTCE VPAQPSPQIH WMKDQVPLPL PPSPVLILPE IGPQDQGTYS
301  CVATHSSHGP QESRAVSISI IEPGEEGPTA GSVGGSGLGT LALAASTKGP
351  SVFPLAPCSR STSESTAALG CLVKDYFPEP VTVSWNSGAL TSGVHTFPAV
401  LQSSGLYSLS SVVTVPSSSL GTKTYTCNVD HKPSNTKVDK RVESKYGPPC
451  PSCPAPEFLG GPSVFLFPPK PKDTLMISRT PEVTCVVVDV SQEDPEVQFN
501  WYVDGVEVHN AKTKPREEQF NSTYRVVSVL TVLHQDWLNG KEYKCKVSNK
551  GLPSSIEKTI SKAKGQPREP QVYTLPPSQE EMTKNQVSLT CLVKGFYPSD
601  IAVEWESNGQ PENNYKTTPP VLDSDGSFFL YSRLTVDKSR WQEGNVFSCS
651  VMHEALHNHY TQKSLSLSLG K
```

Bold text is the amino acid sequence for the RAGE signal sequence, normal text is the amino acid sequence for human RAGE variant, bold wavy underline letters are sites of the point mutations introduced into the variant hRAGE, and underlined text is the amino acid sequence for IgG4 Fc region.

TABLE 7

Human RAGE variant-Linker-IgG4 Fc Fusion Gene Sequence.

(SEQ ID NO: 7)
ATGGCAGCCGGAACAGCAGTTGGAGCCTGGGTGCTGGTCCTCAGTCT

GTGGGGGGCAGTAGTAGGTGCTCAAAACATCACAGCCCGGATTGGCG

TABLE 7-continued

Human RAGE variant-Linker-IgG4 Fc Fusion Gene Sequence.

AGCCACTGGTGCTGAAGTGTAAGGGGGCCCCCAAGAAACCACCCCAG

CGGCTGGAATGGAAACTGAACACAGGCCGGACAGAAGCTTGGAAGGT

CCTGTCTCCCAGGGAGGAGGCCCCTGGGACAGTGTGGCTCGTGTCC

TTCCCAACGGCTCCCTCTTCCTTCCGGCTGTCGGGATCCAGGATGAG

GGGATTTTCCGGTGCCAGGCAATGAACAGGAATGGAAAGGAGACCAA

GTCCAACTACCGAGTCCGTGTCTACCAGATTCCTGGGAAGCCAGAAA

TTGTAGATTCTGCCTCTGAACTCACGGCTGGTGTTCCCAATAAGGTG

GGGACATGTGTGTCAGAGGGAAGCTACCCTGCAGGGACTCTTAGCTG

TABLE 7-continued

Human RAGE variant-Linker-IgG4 Fc Fusion Gene Sequence.

GCACTTGGATGGGAAGCCCCTGGTGCCGAATGAGAAGGGAGTATCTG

TGAAGGAACAGACCAGGAGACACCCTGAGACAGGGCTCTTCACACTG

CAGTCGGAGCTAATGGTGACCCCAGCCCGGGGAGGAGATCCCCGTCC

CACCTTCTCCTGTAGCTTCAGCCCAGGCCTTCCCCGACGCCGGGCCT

TGCACACAGCCCCCATCCAGCCCCGTGTCTGGGAGCCTGTGCCTCTG

GAGGAGGTCCAATTGGTGGTGGAGCCAGAAGGTGGAGCAGTAGCTCC

TGGTGGAACCGTAACCCTGACCTGTGAAGTCCCTGCCCAGCCCTCTC

TABLE 7-continued

Human RAGE variant-Linker-IgG4 Fc Fusion Gene Sequence.

CTCAAATCCACTGGATGAAGGATGGTGTGCCCTTGCCCCTTCCCCCC

AGCCCTGTGCTGATCCTCCCTGAGATAGGGCCTCAGGACCAGGGAAC

CTACAGCTGTGTGGCCACCCATTCCAGCCACGGGCCCCAGGAAAGCC

GTGCTGTCAGCATCAGCATCATCGAACCAGGCGAGGAGGGGCCAACT

GCAGGCTCTGTGGGAGGATCAGGGCTGGGAACTCTAGCCCTGGCC<u>GG</u>

<u>TAGCGGCTCCGGAAGTGGG</u>GCTTCCACCAAGGGCCCATCCGTCTTCC

CCCTGGCGCCCTGCTCCAGGAGCACCTCCGAGAGCACAGCCGCCCTG

GGCTGCCTGGTCAAGGACTACTTCCCCGAACCGGTGACGGTGTCGTG

GAACTCAGGCGCCCTGACCAGCGGCGTGCACACCTTCCCGGCTGTCC

TACAGTCCTCAGGACTCTACTCCCTCAGCAGCGTGGTGACCGTGCCC

TCCAGCAGCTTGGGCACGAAGACCTACACCTGCAACGTAGATCACAA

GCCCAGCAACACCAAGGTGGACAAGAGAGTTGAGTCCAAATATGGTC

CCCCATGCCCATCATGCCCAGCACCTGAGTTCCTGGGGGGACCATCA

GTCTTCCTGTTCCCCCCAAAACCCAAGGACACTCTCATGATCTCCCG

GACCCCTGAGGTCACGTGCGTGGTGGTGGACGTGAGCCAGGAAGACC

CCGAGGTCCAGTTCAACTGGTACGTGGATGGCGTGGAGGTGCATAAT

GCCAAGACAAAGCCGCGGGAGGAGCAGTTCAACAGCACGTACCGTGT

GGTCAGCGTCCTCACCGTCCTGCACCAGGACTGGCTGAACGGCAAGG

AGTACAAGTGCAAGGTCTCCAACAAAGGCCTCCCGTCCTCCATCGAG

AAAACCATCTCCAAAGCCAAAGGGCAGCCCCGAGAGCCACAGGTGTA

CACCCTGCCCCCATCCCAGGAGGAGATGACCAAGAACCAGGTCAGCC

TGACCTGCCTGGTCAAAGGCTTCTACCCCAGCGACATCGCCGTGGAG

TGGGAGAGCAATGGGCAGCCGGAGAACAACTACAAGACCACGCCTCC

CGTGCTGGACTCCGACGGCTCCTTCTTCCTCTACAGCAGGCTAACCG

TGGACAAGAGCAGGTGGCAGGAGGGGAATGTCTTCTCATGCTCCGTG

ATGCATGAGGCTCTGCACAACCACTACACACAGAAGAGCCTCTCCCT

GTCTCTCGGGAAATGA

Bold text is the coding sequence for the RAGE signal sequence, normal text is the coding sequence for human RAGE variant, bold wavy underline letters are sites of the point mutations introduced into the variant hRAGE sequence, double underline text is the sequence encoding a peptide linker, and underlined text is the coding sequence for IgG4 Fc region.

TABLE 8

Amino acid sequence of human RAGE variant-Linker-IgG4 Fc.

(SEQ ID NO: 8)

```
  1 MAAGTAVGAW VLVLSLWGAV VGAQNITARI GEPLVLKCKG APKKPPQRLE

51 WKLNTGRTEA WKVLSPQGGG PWDSVARVLP NGSLFLPAVG IQDEGIFRCQ

101 AMNRNGKETK SNYRVRVYQI PGKPEIVDSA SELTAGVPNK VGTCVSEGSY

151 PAGTLSWHLD GKPLVPNEKG VSVKEQTRRH PETGLFTLQS ELMVTPARGG

201 DPRPTFSCSP SPGLPRRRAL HTAPIQPRVW EPVPLEEVQL VVEPEGGAVA

251 PGGTVTLTCE VPAQPSPQIH WMKDGVPLPL PSPVLILPE IGPQDQGTYS

301 CVATHSSHGP QESRAVSISI IEPGEEGPTA GSVGGSGLGT LALAGSGSGS

351 GASTKGPSVF PLAPCSRSTS ESTAALGCLV KDYFPEPVTV SWNSGALTSG

401 VHTFPAVLQS SGLYSLSSVV TVPSSSLGTK TYTCNVDHKP SNTKVDKRVE

451 SKYGPPCPSC PAPEFLGGPS VFLFPPKPKD TLMISRTPEV TCVVVDVSQE

501 DPEVQFNWYV DGVEVHNAKT KPREEQFNST YRVVSVLTVL HQDWLNGKEY

551 KCKVSNKGLP SSIEKTISKA KGQPREPQVY TLPPSQEEMT KMQVSLTCLV

601 KGFYPSDIAV EWESNGQPEN NYKTTPPVLD SDGSFFLYSR LTVDKSRWQE

651 GNVFSCSVMH EALHNHYTQK SLSLSLGK
```

Bold text is the amino acid sequence for the RAGE signal sequence, normal text is the amino acid sequence for human RAGE variant, bold wavy underline letters are sites of the point mutations introduced into the variant hRAGE, double underline text is the amino acid sequence for the peptide linker, and underlined text is the amino acid sequence for IgG4 Fc region.

Expression of Rage Fusion Proteins

Fusion proteins of the invention may be produced in any protein expression system known to those skilled in the art, for example, eukaryotic expression systems, bacterial expression systems, and viral expression systems. A variety of host-expression vector systems may be utilized to express the fusion protein of the invention. Such host systems represent vehicles in which the fusion proteins of the invention may be produced and from which they may be subsequently purified. Such systems include, but are not limited to microorganisms such as bacteria, yeast, insect cells, or plant cells. RAGE expressed in yeast or mammalian expression systems, e.g., COS-7 cells, may be similar or slightly different in molecular weight and glycosylation pattern than the native molecules, depending upon the expression system. Expression of RAGE DNAs in bacteria such as E. coli provides non-glycosylated molecules. Different glycosylation patterns may be obtained using baculoviral expression systems in insect cells. Functional mutant analogs of mammalian RAGE having inactivated N-glycosylation sites can be produced by oligonucleotide synthesis and ligation at by site-specific mutagenesis techniques. These analog proteins can be produced in a homogeneous, reduced-carbohydrate form in good yield using yeast expression systems.

Nucleic acid molecules encoding fusion proteins of the invention may be obtained, and the nucleotide sequence of the polynucleotides determined, by any method known in the art. In view of the teachings herein and the known RAGE polypeptide sequences and their identified or identifiable ligand binding elements, and the known sequences for heavy chain IgG constant domains, nucleotide sequences encoding these polypeptides can be determined using methods well known in the art, i.e. the nucleotide codons known to encode the particular amino acids may be assembled in such a way to generate a nucleic acid that encodes the fusion protein of the invention. Nucleotide codons may be selected based upon the expression system used, for example, by selecting codons that correspond to more abundant tRNA molecules present in the expression system, a higher level of fusion protein may be expressed. Such a polynucleotide encoding the fusion protein may be assembled from chemically synthesized oligonucleotides (e.g. as described in Kutmeier et. Al., Biotechniques 17:242 (1994), which, briefly, involves the synthesis of overlapping oligonucleotides containing portions of the sequence encoding the fusion protein, annealing and ligating of those oligonucleotides, and then amplification of the ligated oligonucleotides by polymerase chain reaction(s) (PCR).

Recombinant expression of as fusion protein of the invention (including other molecules comprising or alternatively consisting of fusion protein fragments or variants thereof) may require construction of an expression vector(s) containing a polynucleotide that encodes the fusion protein. Once a polynucleotide encoding the fusion protein of the invention has been obtained, the vector(s) for the production of the fusion protein may be produced by recombinant DNA technology using techniques well known in the art. Such expression vectors containing RAGE-Fc coding sequences may also contain appropriate transcriptional and translational control signals/sequences, for example, ribosome binding sites (i.e., Kozak sequences), internal ribosome entry sites (IRES), and polyadenylation sites etc.

Nucleic acid molecules encoding fusion proteins of the invention may be transferred to mammalian cells utilizing replication-defective retroviral vectors (e.g., vectors derived from Moloney murine leukemia virus (MLV) or HIV) and pseudotyped with vesicular stomatitis virus G protein (VSV-G) to stably insert single copies of nucleic acid molecules encoding the fusion protein of the invention into dividing cells. Retroviral vectors deliver genes coded as RNA that, after entering the cell, are reverse transcribed to DNA and integrated stably into the genome of the host cell. Multiple gene insertions in a single cell may increase the expression and secretion of the fusion protein. Multiple rounds of infection may also increase the number of gene copies integrated and thus the amount of expressed fusion protein. The integrated gene(s) encoding the fusion protein are maintained in the cells through cell division by virtue of their presence in the genome.

In some embodiments, the present invention provides a stable cell line that expresses fusion proteins of the invention. One suitable method for the rapid generation of stable, high protein expressing mammalian cell lines is using the GPEx™ expression system (Gala Biotech, a business unit of Catalent Pharma Solutions, Middleton, Wis., Bleck, Gregory T., Bio-processingjournal.com September/October 2005 p1-7). Such a method may entail producing a replication defective, pseudotyped retroviral vector based on MMLV and transducing mammalian cells (for example, CHO cells) with the vector. The vector may integrate into the genome of the cells thereby producing a stable cell line.

Purification of Isolated Fusion Protein

Isolated fusion proteins of the invention may be prepared by culturing suitable host/vector systems to express the recombinant translation products of the present DNA sequences, which are then purified from culture media or cell extracts using techniques well known in the art.

For example, supernatants from systems which secrete recombinant protein into culture media can be first concentrated using a commercially available protein concentration filter, for example, an Amicon or Millipore Pellicon ultra filtration unit. Following the concentration step, the concentrate can be applied to a suitable purification matrix. For example, a suitable affinity matrix can comprise, for example, an AGE or lectin or Protein A or Protein G or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising, sulfopropyl or carboxymethyl groups. Sulfopropyl groups are preferred.

Recombinant protein produced in bacterial culture is usually isolated by initial extraction from cell pellets, followed by one or more concentration, salting-out, aqueous on exchange or size exclusion chromatography steps. Finally, high performance liquid chromatography (HPLC) can be employed for final purification steps. Microbial cells employed in expression of recombinant mammalian RAGE can be disrupted by any convenient method, including freeze-thaw cycling, sonication, mechanical disruption, or use of cell lysing agents.

Fermentation of yeast which expresses the fusion protein of the invention as a secreted protein greatly simplifies purifications. Secreted recombinant protein resulting from a large-scale fermentation can be purified by methods analogous to those disclosed by Urdal et al. (J. Chromatog. 296: 171, 1984). This reference describes two sequential, reversed-phase HPLC steps for purification of recombinant human GMCSF on a preparative HPLC column.

Pharmaceutical Compositions

Fusion proteins of the invention may be formulated in it manner suitable for administration to a subject in need thereof, e.g., may be formulated as pharmaceutical compositions. Compositions of the invention may comprise one or more pharmaceutically-acceptable carrier, excipient or diluent. As used herein "pharmaceutically-acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. A carrier may be suitable for administration into the central nervous system (e.g., intraspinally or intracerebrally). Alternatively, the carrier can be suitable for intravenous, subcutaneous, intraperitoneal or intramuscular administration. In another embodiment, the carrier is suitable for oral administration. Pharmaceutically-acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the fusion proteins of the invention, use thereof in the pharmaceutical compositions of the invention is contemplated. Supplementary active compounds can also be incorporated into the compositions.

Suitable carriers are typically nontoxic to recipients at the dosages and concentrations employed. Ordinarily, the preparation of pharmaceutical compositions of the invention entails combining the fusion protein of the invention with one or more of buffers, antioxidants such as ascorbic acid, low molecular weight (less than about 10 residues) polypeptides, proteins, amino acids, carbohydrates including glucose, trehalose, sucrose or dextrins, chelating agents such as EDTA, glutathione and other stabilizers and excipients. Neutral buffered saline or saline mixed with conspecific serum albumin are exemplary appropriate diluents.

Therapeutic Administration of Fusion Proteins of the Invention

The present invention contemplates the administration of the fusion proteins of the invention in the form of a pharmaceutical composition comprising the fusion protein of the invention and a pharmaceutically acceptable diluent or carrier to a subject (e.g., a mammal particularly a human) in need thereof. The present invention also provides a method for treating human disease with such compositions.

Typically, methods of the invention will comprise administering a pharmaceutical composition comprising a pharmaceutically effective amount of a fusion protein of the invention. The pharmaceutically effective amount employed may vary according to factors such as the disease state, age, sex, and weight of the individual.

A pharmaceutically effective amount of a fusion protein of the invention may be from about 1 µg fusion protein/1 kg body weight of subject to about 500 mg fusion protein/1 kg body weight of subject, or from about 10 µg fusion protein/1 kg body weight of subject to about 500 mg fusion protein/1 kg body weight of subject, or from about 10 mg fusion protein/1 kg body weight of subject to about 500 mg fusion protein/1 kg body weight of subject, or from about 100 mg fusion protein/1 kg body weight of subject to about 500 mg fusion protein/1 kg body weight of subject, or from about 10 mg fusion protein/1 kg body weight of subject to about 500 mg fusion protein/1 kg body weight of subject, or from about 100 mg fusion protein/1 kg body weight of subject to about 500 mg fusion protein/1 kg body weight of subject, or from about 100 µg fusion protein/1 kg body weight of subject to about 25 mg fusion protein/1 kg body weight of subject, or from about 1 mg fusion protein/1 kg body weight of subject to about 25 mg fusion protein/1 kg body weight of subject, or from about 5 mg fusion protein/1 kg body weight of subject to about 25 mg fusion protein/1 kg body weight of subject, or from about 10 mg fusion protein/1 kg body weight of subject to about 25 mg fusion protein/1 kg body weight of subject, or from about 15 mg fusion protein/1 kg body weight of subject to about 25 mg fusion protein/1 kg body weight of subject, or from about 100 µg fusion protein/1 kg body weight of subject to about 10 mg fusion protein/1 kg body weight of subject, or from about 1 mg fusion protein/1 kg body weight of subject to about 10 mg fusion protein/1 kg body weight of subject, or from about 2.5 mg fusion protein/1 kg body weight of subject to about 10 mg fusion protein/1 kg body weight of subject, or from about 5 mg fusion protein/1 kg body weight of subject to about 10 mg fusion protein/1 kg body weight of subject, or from about 7.5 mg fusion protein/1 kg body weight of subject to about 10 mg fusion protein/1 kg body weight of subject.

In some embodiments, a pharmaceutically effective amount of a fusion protein of the invention may be 0.5 mg fusion protein/1 kg body weight of subject, 1 mg fusion protein/1 kg body weight of subject, 2 mg fusion protein/1 kg body weight of subject, 3 mg fusion protein/1 kg body weight of subject, 4 mg fusion protein/1 kg body weight of subject, 5 mg fusion protein/1 kg body weight of subject, 6 mg fusion protein/1 kg body weight of subject, 7 mg fusion protein/1 kg body weight of subject, 8 mg fusion protein/1 kg body weight of subject, 9 mg fusion protein/1 kg body weight of subject, or 10 mg fusion protein/1 kg body weight of subject.

A unit dosage form refers to physically discrete units suited as unitary dosages for the mammalian subjects to be treated; each unit containing a predetermined quantity of the fusion protein of the invention calculated to produce the desired therapeutic effect in association with the required pharmaceutical carrier. A unit dosage form of a fusion protein of the invention may be from about 1 mg to about 1000 mg, from about 25 mg to about 1000 mg, from about 50 mg to about 1000 mg, from about 100 mg to about 1000 mg, from about 250 mg to about 1000 mg, from about 500 mg to about 1000 mg, from about 100 mg to about 500 mg, from about 200 mg to about 500 mg, from about 300 to about 500 mg, or from about 400 mg to about 500 mg. A unit dose of a fusion protein of the invention may be about 100 mg, 200 mg, 300 mg, 400 mg, 500 mg, 600 mg, or 700 mg.

Compositions of the invention may comprise fusion proteins of the invention at a level of from about 0.1 wt % to about 20 wt %, from about 0.1 wt % to about 18 wt %, from about 0.1 wt % to about 16 wt %, from about 0.1 wt % to about 14 wt %, from about 0.1 wt % to about 12 wt %, from about 0.1 wt % to about 10 wt %, from about 0.1 wt % to about 8 wt %, from about 0.1 wt % to about 6 wt % from about 0.1 wt % to about 4 wt %, from about 0.1 wt % to about 2 wt %, from about 0.1 wt % to about 1 wt %, from about 0.1 wt % to about 0.9 wt %, from about 0.1 wt % to about 0.8 wt %, from about 0.1, wt % to about 0.7 wt %, from about 0.1 wt % to about 0.6 wt %, from about 0.1 wt % to about 0.5 wt %, from about 0.1 wt % to about 0.4 wt %, from about 0.1 wt % to about 0.3 wt %, or from about 0.1 wt % to about 0.2 wt % of the total weight of the composition.

Pharmaceutical compositions of the invention may comprise one or more fusion proteins of the invention at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 9 wt %, from about 1 wt % to about 8 wt %, from about 1 wt % to about 7 wt %, from about 1 wt % to about 6 wt %, from about 1 wt % to about 5 wt %, from about 1 wt % to about 4 wt %, from about 1 wt % to about 3 wt %, or from about 1 wt % to about 2 wt % of the total weight of the composition. Pharmaceutical compositions of the invention may comprise one or more fusion proteins of the invention at a level of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 about 5 wt %, about 6 wt %, about 7 wt %, about 8 wt %, or about 9 wt % based on the total weight of the composition.

Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Compositions of the invention may be formulated and administered by intravenous, intramuscular, or subcutaneous injection. In some embodiments, compositions of the invention may be administered subcutaneously or intramuscularly.

In some embodiments a dosage regimen may entail administering repeat doses, for example, administering a weekly dose. Treatment regimens may entail a weekly dose for one period of time (for example, for four weeks) followed by a less frequent "maintenance" dosage regimen (for example, one monthly or once bimonthly). Dosage regimens may be adjusted to achieve the desired therapeutic outcomes.

Methods of the invention include methods for suppressing AGE-dependent inflammatory responses in humans composing administering an effective amount of a pharmaceutical composition comprising one or more fusion protein of the invention.

Methods of the invention include methods of inhibiting AGE-mediated biological activity comprising administering a pharmaceutical composition comprising one or more fusion proteins of the invention. As discussed above, AGE has been implicated in a variety of diseases or conditions such as autoimmune diseases. Autoimmune disorders diseases or conditions that may be treated, ameliorated, detected, diagnosed, prognosed or monitored using the fusion protein of the invention include but are not limited to dermatitis, glomerulonephritis, multiple sclerosis, uveitis ophthalmia, autoimmune pulmonary inflammation, insulin dependent diabetes mellitus, autoimmune inflammatory eye, systemic lupus erythematosus, insulin resistance, rheumatoid arthritis, diabetic retinopathy, and scleroderma.

Other disorders that may be treated or prevented with the methods of the invention may be characterized generally as including any disorder in which an affected cell exhibits elevated expression of RAGE or of one or more RAGE ligands, or any disorder that is treatable (i.e., one or more symptoms may be eliminated or ameliorated) by a decrease in RAGE function. For example, RAGE function can be decreased by administration of an agent that disrupts the interaction between RAGE and a RAGE ligand.

The increased expression of RAGE is associated with several pathological states, such as diabetic vasculopathy, nephropathy, retinopathy, neuropathy, and other disorders, including Alzheimer's disease and immune/inflammatory reactions of blood vessel walls. RAGE ligands are produced in tissue affected with many inflammatory disorders, including arthritis (such as rheumatoid arthritis). Depositions of amyloid in tissues cause a variety of toxic effects on cells and are characteristic of diseases termed amyloidoses. RAGE binds to beta-sheet fibrillar material, such as that found in amyloid-beta peptide, Abeta, amylin, serum amyloid A and prion-derived peptides. RAGE is also expressed at increased levels in tissues having amyloid structures. Accordingly, RAGE is involved in amyloid disorders. The RAGE-amyloid interaction is thought to result in oxidative stress leading to neuronal degeneration.

A variety of RAGE ligands, and particularly those of the S100/calgranulin and Amphoterin (HMGB) families are produced in inflamed tissues. This observation is true both for acute inflammation, such as that seen in response to a lipopolysaccharide challenge (as in sepsis) and for chronic inflammation, such as that seen in various forms of arthritis, ulcerative colitis, inflammatory bowel disease, etc. Cardiovascular diseases, and particularly those arising from atherosclerotic plaques, are also thought to have a substantial inflammatory component. Such diseases include occlusive, thrombotic and embolic diseases, such as angina, fragile plaque disorder and embolic stroke, respectively. Tumor cells also evince an increased expression of a RAGE ligand, particularly amphoterin, indicating that cancers are also a RAGE-related disorder. Furthermore, the oxidative effects and other aspects of chronic inflammation may have a contributory effect to the genesis of certain tumors.

AGE are a therapeutic target for rheumatoid arthritis and other inflammatory diseases.

Accordingly, the RAGE-related disorders that may be treated with an inventive compositions include, in addition to the autoimmune disorders discussed above: amyloidoses (such as Alzheimer's disease), Crohn's disease, acute inflammatory diseases (such as sepsis), shock (e.g., septic shock, hemorrhagic shock), cardiovascular diseases (e.g., atherosclerosis, stroke, fragile plaque disorder, angina and restenosis), diabetes (and particularly cardiovascular diseases in diabetics), complications of diabetes, prion-related disorders, cancers, vasculitis and other vasculitis syndromes such as necrotizing vasculitides, nephropathies, retinopathies, and neuropathies.

The following examples are provided for illustrative purposes only, and are in no way intended to limit the scope of the present invention.

EXAMPLES

In the following examples, experiments in mice were performed with a fusion protein comprising extracellular domains of mouse RAGE (amino acid residues 1-342) fused to the hinge, CH2 and CH3 domains of the mouse IgG2a heavy chain FC region. The construct was expressed in CHO cells using the GPEx™ expression system. The sequence of the mouse RAGE sequence used is provided in the following table.

TABLE 9

Sequence of mouse RAGE (SEQ ID NO: 11)
<u>MPAGTAARAW VLVLALWGAV AGGQNITARI</u> GEPLVLSCKG

APKKPPQQLE WKLNTGRTEA WKLVSPQGGP WDSVARILPN

GSLLLPATGI VDEGTFRCRA TNRRGKEVKS NYRVRVYQIP

GKPEIVDPAS ELTASVPNKV GTCVSEGSYP AGTLSWHLDG

KLLIPDGKET LVKEETRRHP ETGLFTLRSE LTVIPTQGGT

HPTFSCSFSL GLPRRRPLNT APIQLRVREP GPPEGIQLLV

EPEGGIVAPG GTVTLTCAIS AQPPPQVHWI KDGAPLPLAP

SPVLLLPEVG HEDEGTYSCV ATHPSHGPQE SPPVSIRVTE

TGDEGPAEGS VGESGLGTLA LA<u>EPRGPTIK PCPPCKCPAP

NLLGGPSVFI FPPKIKDVLM ISLSPIVTCV VVDVSEDDPD

VQISWFVNNV EVHTAQTQTH PEDYNSTLRV VSALPIQHQD

WMSGKEFKCK VNNKDLPAPI ERTISKPKGS VRAPQVYVLP

PPEEEMTKKQ</u> VTLTCMVTDP MPEDIQVEWT NNGKTELNYK

NTEPVLDSDG SYFMYSKLRV EKKNWVERNS YSCSVVHEGL

HNHHTTKSFS RTPGK where RAGE signal peptide=plain underline, RAGE extracellular domain=no underline, Mouse IgG2a hinge region=double underline, Mouse IgG2a CH2 region=dash underline, and Mouse IgG2a CH3 region=wavy underline.

Example 1

Effect of Rage Fusion Proteins of the Invention on Streptozotocin Induced Diabetes in Mice Streptozotocin induced diabetes in mice is an art recognized model for diabetes induced retinal changes (see Obrosova I G, Drel V R, Kumagai A K, Szabo C, Pacher P, Stevens M J. Early diabetes-induced biochemical changes in the retina: comparison of rat and mouse models. *Diabetologia.* 2006 October: 49(10):2525-33.)

The present experiment involved 5 treatment groups containing 15 C57BL/6 mice per group; 1) non-diabetic control; 2) diabetic control containing mice treated with streptozotocin at 45 mg/kg on 5 consecutive days before the study starts to induce diabetes; 3) streptozotocin treated mice that also received 10 μg/day mRAGE-IgG2aFc injected IP, 3 injections/week; 4) streptozotocin treated mice that also received 100 μg/day mRAGE-IgG2aFc injected IP, 3 injections/week; and 5) streptozotocin treated mice that also received 300 μg/day mRAGE-IgG2aFc injected IP, 3 injections/week.

During the study, the truce were assessed for body weight, blood glucose, glycohemoglobin (GHb), albuminuria, and tactile sensitivity as measure of sensor nerve function. The mice were sacrificed at the end of the study and assessed for retinal vascular permeability using a fluorescent probe, leukocyte adherence to retinal capillaries, and NF-kB-regulated protein expression (COX-2, ICAM, iNOS).

Results from Two Month Long Study

The effects of RAGE-Ig fusion protein on the development of diabetes-induced alterations in retinal physiology and metabolism in C57Bl/6J mice were studied. The fusion protein was administered intraperitoneally at 3 different concentrations (10 μg, 100 μg, and 300 μg) three times per week. No adverse effects of any dose of drug on body weight gain or overall health of the diabetic mice was seen. Nonfasted blood glucose levels were 155±24 mg/dl (mean±SD), 358±38, 417±36, 376±36, and 370±55 in the Non-diabetic control, Diabetic control, Diabetic+10 μg RAGE-Ig fusion protein, Diabetic+100 μg RAGE-Ig fusion protein, and Diabetic+300 μg RAGE-Ig fusion protein groups, respectively.

Parameters related to retinopathy measured in the short-term studies were (1) leukostasis, (2) permeability of endogenous albumin from retinal vessels, (3) nitration of retinal proteins, and (4) expression of retinal ICAM and COX-2.

1. Leukostasis.

Methods: At 2 months of diabetes, blood was removed from the vasculature of anesthetized animals by complete perfusion with PBS via a heart catheter. Animals then were perfused with fluorescein-coupled Concanavalin A lectin (20 μg/ml in PBS; Vector Laboratories, Burlingame, Calif.) as described previously (see Joussen et al., *FASEB J.* 2004 September; 18(12):1450-2). Fiat-mounted retinas were imaged via fluorescence in microscopy, and the number of leukocytes adherent to the vascular wall was counted.

Results: A significant increase in leukostasis was demonstrated in mice that had been diabetic for 2 months compared to the nondiabetics (P<0.05). Leukostasis was not inhibited in any of the groups treated with the RAGE-Ig fusion protein (see FIG. 1).

2. Vascular Permeability

Methods: At 2 months of diabetes, eyes were cryosectioned (10 μm), fixed in methanol for 10 min, and washed 4× in PBS. Each section was incubated in sheep anti-mouse serum albumin (Abcam, Cambridge Mass.; AB8940; 1:2000 dilution) for 2 hrs. After washing, sections were incubated in FTIC-labeled secondary antibody (AB 6743; 1:1000 dilution) for 90 min. Under fluorescence microscopy, the average amount of fluorescence was determined in 3 different sites for each of 4 retinal layers (inner plexiform layer, inner nuclear layer, outer plexiform layer, outer nuclear layer). The amount of fluorescence in each site was the average of 10 random measurements, and the amount of fluorescence in each retinal layer was the average of fluorescence in each of the 3 different sites within that layer.

Results:

Diabetes resulted in a significant increase in the fluorescence in the nonvascular retina (ie, due to albumin leaking out of the vessels) in each of the 4 retinal layers studied. The results are shown in FIG. 2 (2A inner plexiform layer, 2B inner nuclear layer, 2C outer plexiform layer, 2D outer nuclear layer). To assess albumin in the inner and outer nuclear layers, we intentionally measured in the thin space between nuclei, so these numbers might not be as strong as those from the plexiform where there were no nuclei to impair our measurements.

3. Nitration of Retinal Proteins

Methods: At 2 months of diabetes, retinas were isolated and homogenized. Dot-blots were made, blotting 50 μg protein homogenate from each animal onto nitrocellulose membrane. Membranes were blocked with milk (5%), washed, and immunostained using anti-nitrotyrosine (Upstate Biotechnology, Inc. #05-233; 1:500 dilution) for 2 hrs, and then stained with secondary antibody (Bio-Rad goat anti-mouse IgG-HRP conjugate; 1:1000 dilution) for 1 hour. After extensive washing, immunostaining detected by the antibody was visualized by enhanced chemiluminescence (ECL, Santa Cruz Biotechnology, Santa Cruz, Calif.). Immunostain-dependent chemiluminescence was recording on film, and the density of the immunostained dots quantitated. Results are expressed as a percent of values detected in the nondiabetic controls.

Figure 3:
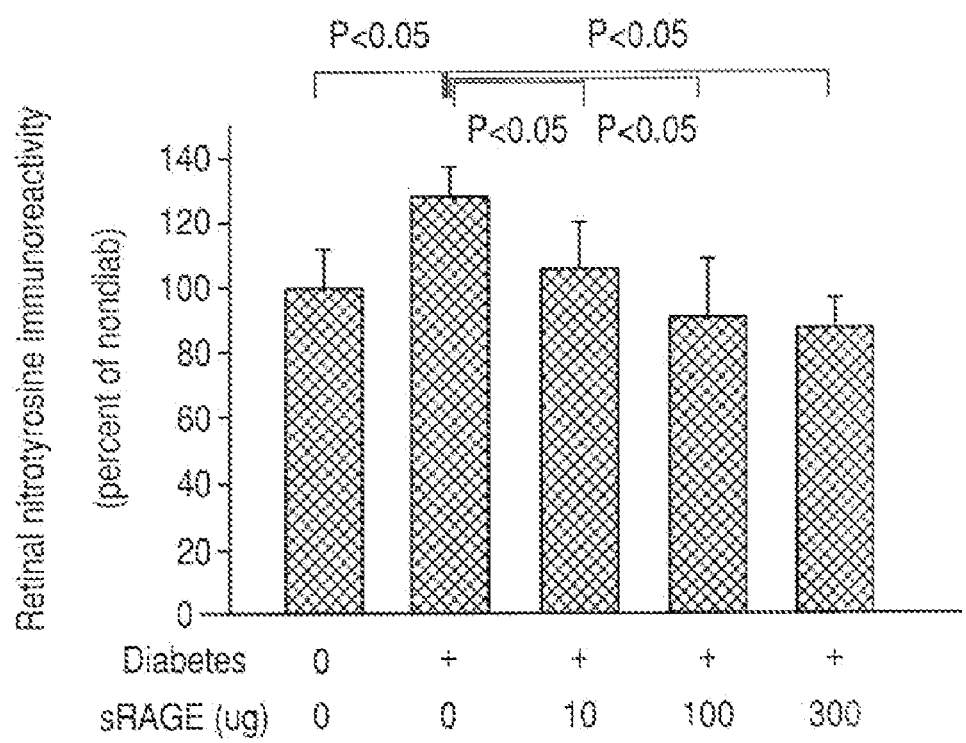
FIG. 3 is a bar graph showing the effects of an exemplary RAGE-Ig fusion protein on the nitration of retinal proteins in a streptozotocin-induced diabetic mouse model.

Results:

Results are shown in FIG. 3. Retinal homogenates from diabetic mice showed the expected increase in nitration of proteins. The therapy inhibited this post-translational modification in a dose-dependent manner. Nitration of proteins is regarded to be a parameter of both oxidative and nitrative stress.

4. Expression of Retinal ICAM and COX-2

Methods: Retinas were isolated and sonicated, and the supernatant used as whole retinal extract. Samples (50 μg) were fractionated by SDS-PAGE, electroblotted to nitrocellucose membrane, and membranes blocked in Tris-buffered saline containing 0.02% Tween 20 and 5% nonfat milk. Antibodies for ICAM-1 (1:200 dilution; Santa Cruz Biotechnology) and COX-2 were applied, followed by secondary antibody for 1 hour. After washing, results were visualized by enhanced chemiluminescence.

Figure 4:
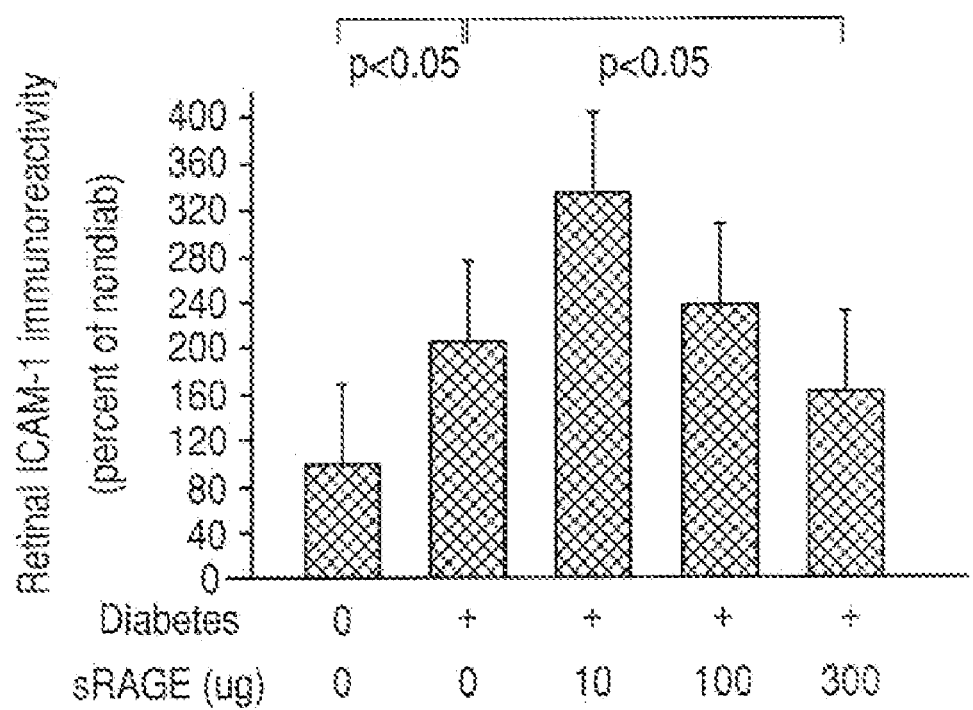
FIG. 4 is a bar graph showing the effects of an exemplary RAGE-Ig fusion protein on the retinal expression of ICAM in a streptozotocin-induced diabetic mouse model.

Results:

Results are shown in FIG. 4. Since ICAM-1 expression on endothelial cells plays a critical role in adhesion of white blood cells to the vessel wall (leukostasis), we measured the effect of diabetes and the therapy on expression of ICAM-1 in retina. Two months of diabetes did result in a significant increase in expression of retinal ICAM-1. Administration of the RAGE-Ig fusion protein resulted in a dose-dependent decrease in expression of the ICAM, and the highest dose significantly inhibited this expression.

Expression of an immunostained band consistent with the molecular weight for COX-2 did not increase in diabetes and did not change in animals getting the therapy (not shown).

The endpoints use in this short term study of the effects of the RAGE-Ig fusion protein were selected because all have been found to be associated with the development of the early (degenerative) stages of diabetic retinopathy, ie, various therapies that have been found to inhibit diabetes-induced degeneration of retinal capillaries also have inhibited these defects.

Inhibition of RAGE did inhibit abnormalities related to vascular permeability and nitrative stress in the retina. Nitrative stress also is regarded as a marker of oxidative stress. The RAGE inhibitor, however, did not inhibit abnormalities related to leukostasis.

Example 2

Effect of Rage Fusion Proteins of the Invention on Long-Term Streptozotocin Induced Diabetes in Mice Streptozotocin induced diabetes in mice is an art recognized model for diabetes induced retinal changes (see Obrosova I G, Drel V R, Kumagai A K, Szabo C, Pacher P, Stevens M J. Early diabetes-induced biochemical changes in the retina: comparison of rat and mouse models. *Diabetologia*. 2006 October: 49(10):2525-33.)

The long term studies involved 5 treatment groups containing 25 C57BL/6 mice per group: 1) non-diabetic control; 2) diabetic control containing mice treated with streptozotocin at 45 mg/kg on 5 consecutive days before the study starts to induce diabetes; 3) streptozotocin treated mice that also received 10 μg/day mRAGE-IgG2aFc injected IP, 3 injections/week; 4) streptozotocin treated mice that also received 100 μg/day mRAGE-IgG2aFc injected IP, 3 injections/week; and 5) streptozotocin treated mice that also received 300 μg/day mRAGE-IgG2aFc injected IP, 3 injections/week.

During the study, the mice were assessed for body weight, blood glucose, glycohemoglobin (GHb), albuminuria, and tactile sensitivity as measure of sensory nerve function. The mice were sacrificed at the end of the study and assessed for quantitative histopathology and neurodegeneration in the retina.

Parameters related to retinopathy measured in the long-term study were (1) acellular capillaries, (2) pericyte ghosts, and (3) ganglion cells. As a marker of peripheral neuropathy, sensitivity of the paw to light touch was also measured in the long-term study.

Diabetes-Induced Retinal Histopathology

After 10 mos of diabetes, eyes were fixed in formalin, and one retina from each animal was isolated, washed in running water overnight, and digested for 2 hrs in crude trypsin solution as we have reported previously. The retinal vasculature was isolated by gently dislodging neural cells with a "brush" made from a single hair. When totally cleaned of neural cells, the isolated vasculature was laid out on a glass microscope slide, dried overnight, stained with hematoxylin and periodic acid—Schiff, dehydrated and coverslipped. Degenerate (acellular) capillaries were quantitated in 6-7 field areas corresponding to the mid-retina (200× magnification) in a masked manner. Acellular capillaries were identified as capillary-sized vessel tubes having no nuclei anywhere along their length, and were reported per square millimeter of retinal area. Pericyte ghosts were estimated from the prevalence of protruding "bumps" in the capillary basement membranes from which pericytes had disappeared. At least 1,000 capillary cells (endothelial cells and pericytes) in 5 field areas in the mid-retina (400× magnification) in a masked manner were examined. Ghosts on any already acellular vessel were excluded.

To study the effects of diabetes on retinal neurodegeneration, cells in the ganglion cell layer were counted. Formalin-fixed eyes were embedded in paraffin, sectioned sagittally through the retina, going through the optic nerve, and stained with hematoxylin-eosin. The number of cells in the ganglion cell layer were counted in two areas (mid-retina and posterior retina adjacent to optic nerve) on both sides of the optic nerve. Comparable areas from both sides of the optic nerve were averaged, and expressed per unit length.

Figure 5A:
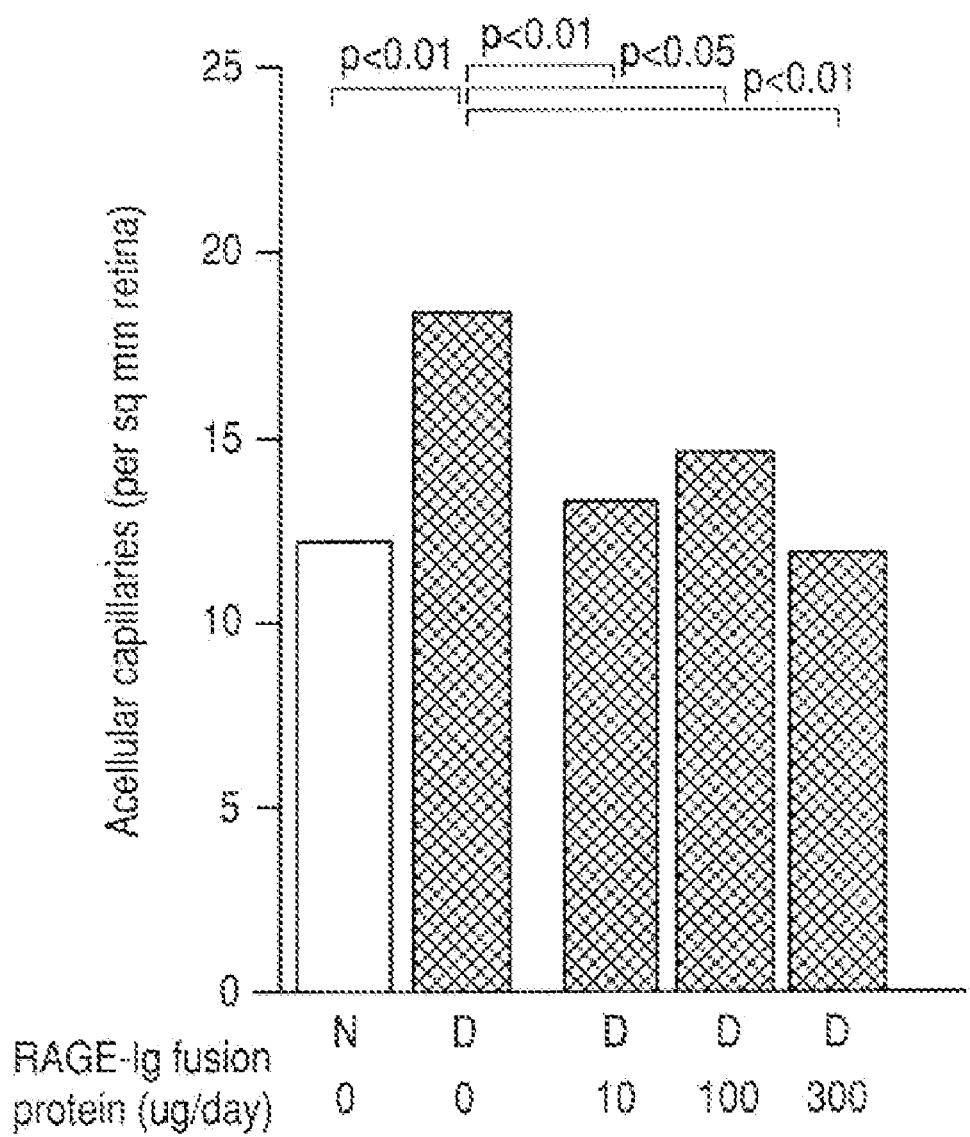
FIG. 5A is a bar graph showing the effects of an exemplary RAGE-Ig fusion protein on the number of acellular capillaries observed per square ram of retinal tissue in diabetic mice after 10 months of diabetes.
Figure 5B:
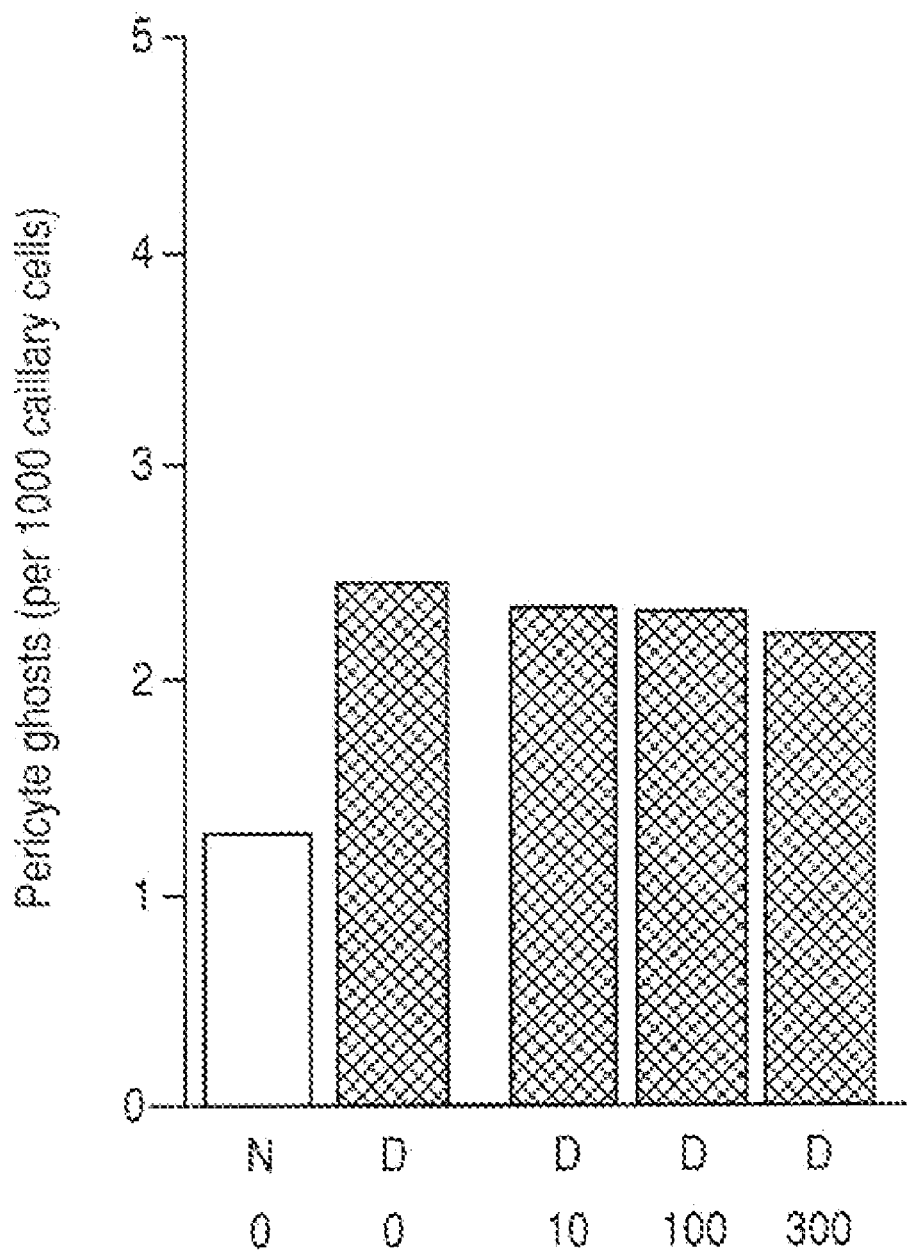
FIG. 5B is a bar graph showing the effects of an exemplary RAGE-Ig fusion protein on the number of pericyte ghosts per 1000 capillary cells observed in diabetic mice after 10 months of diabetes.

Results. As expected base on previous work, long-term diabetes resulted in a significant increase in the number of degenerate, acellular capillaries in the retina (FIG. 5A). All doses of the RAGE-Ig fusion protein significantly inhibited this capillary degeneration, without having any effect on the severity of hyperglycemia. Diabetes also tended to increase pericyte degeneration (pericyte ghosts), but the results did not achieve statistical significance (FIG. 5B). We previously have found pericyte loss to be much more difficult to detect in diabetic C57Bl/6 mice compared to diabetic rats or larger species, and we now regard it as an unreliable parameter of vascular disease in this model. Perhaps as a result of the failure to detect significant pericyte loss in control diabetics, we did not detect any effect of the RAGE-Ig fusion protein on pericyte loss in these mice.

Diabetes did not induce a decrease in the number of cells in the retinal ganglion cell layer (ie, neurodegeneration) in these C57Bl/6 mice. This finding was consistent with a prior study of this mouse model. In the absence of an effect of diabetes on the retinal neurodegeneration, we are unable to assess whether or not the inhibitor would have had an effect on the neurodegeneration.

Sensitivity to Light Touch (a Marker of Peripheral Neuropathy).

Patients with diabetic neuropathy may exhibit a variety of aberrant sensations including spontaneous pain, pain evoked by light touch and hyperalgesia. There is accumulating data that diabetic rodents reproduce this hyperalgesia, and develop a tactile allodynia. In rodents, this is measured as the paw tactile response threshold.

Methods: Mice (8 mos diabetes) were transferred to a testing cage with a wire mesh bottom and allowed to acclimatize for 10 to 15 min. Von Frey filaments were used to determine the 50% mechanical withdrawal threshold for foot withdrawal. A series of filaments with logarithmically increasing stiffness, starting with one that had a buckling weight of 0.6 g, were applied in sequence to the plantar surface of the right hind paw with a pressure that caused the filament to buckle. Lifting of the paw was recorded as a positive response and a lighter filament was chosen for the next measurement. If there was no response after 5 seconds, the next heaviest filament was used afterwards. This method was continued until four measurements had been made after an initial change in the behavior or until five consecutive negative (6 g) or four consecutive positive (0.4 g) responses had occurred. The resulting sequence of positive and negative scores was used to calculate the 50% withdrawal response threshold.

Figure 6:
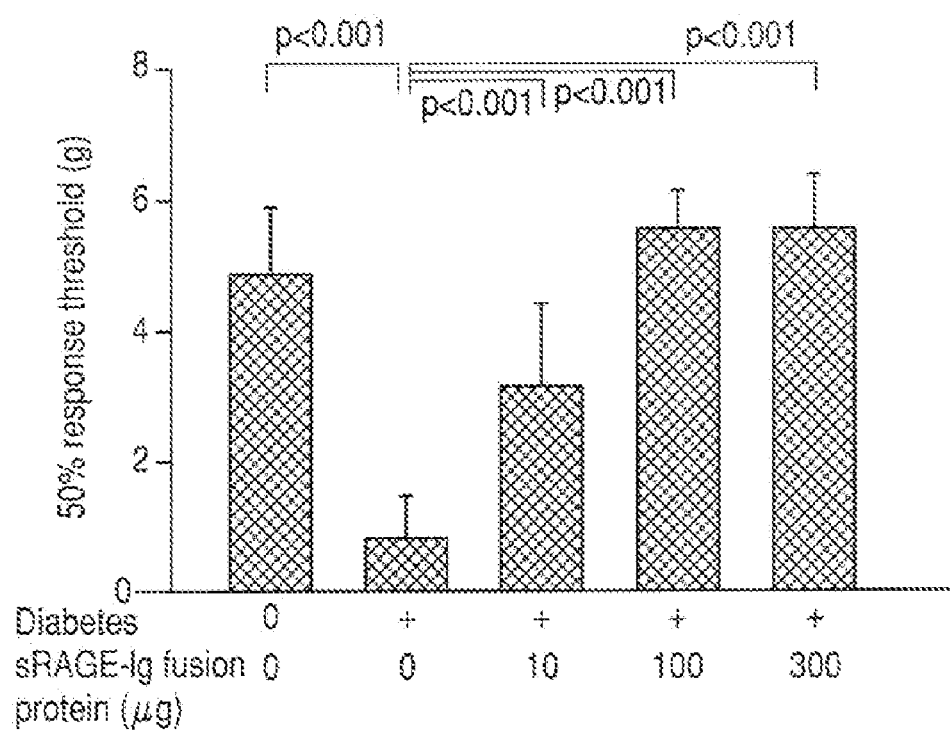
FIG. 6 is a bar graph showing the effects of an exemplary RAGE-Ig fusion protein on the 50% response to touch threshold in diabetic mice after 10 months of diabetes.

Results: Diabetes significantly increased the sensitivity of the paw to light touch, meaning that it required a lower amount of pressure for diabetic animals to withdraw their paw than did nondiabetic animals (FIG. 6). This diabetes-induced defect was significantly inhibited at each dose of the sRAGE-Ig fusion protein.

Retinopathy: The studies conducted using the RAGE-Ig fusion protein were conducted for 2 durations of diabetes: (1) long-term (10 mo) studies to assess the effect of the therapy on long-term histopathology of diabetic retinopathy that develops in mice, and (2) 2-3 mo studies to assess physiologic and molecular effects of the therapy that presumably underlie the effects on long-term histopathology. The physiologic and molecular endpoints studied with respect to effects of the RAGE-Ig fusion protein were selected because all have been found in other studies to be associated with (and likely causally related to) the development of the early (degenerative) stages of diabetic retinopathy. All three doses of the therapy clearly and significantly inhibited the diabetes-induced degeneration of the retinal vasculature. Likewise, all three doses of the drug seemed to inhibit also diabetes-induced increase in retinal permeability in these mice. These findings are of major clinical significance, because the early (nonproliferative) stages of diabetic retinopathy still are defined based on vascular pathology (vascular nonperfusion and degeneration, and increased permeability).

The effect of the therapy on the measured molecular and physiologic endpoints in retinas from diabetic mice was mixed. Inhibition of RAGE did inhibit abnormalities related to nitrative stress, a marker of oxidative stress in the retina. The RAGE inhibitor, however, did not inhibit abnormalities related to leukostasis. The lack of effect of the therapy on leukostasis is surprising in that another group recently reported that their sRAGE did inhibit the increase in leukostasis in diabetes. Evidence that we have generated since the start of our studies using the RAGE-Ig fusion protein (Diabetes 57:1387-93, 2008), however, indicates that effects of a drug therapy on retinal leukostasis in diabetes does not predict the effect of the therapy on the degeneration of retinal capillaries in diabetes. Thus, the lack of the therapy on retinal leukostasis in no way diminishes the significance of the observed effects of the drug.

Surprisingly, there appeared to be a dose effect of the drug with respect to expression of ICAM-1 and nitration of proteins in retinas from the diabetic animals, whereas this dose effect was not apparent on retinal capillary permeability and degeneration. This would seem to suggest that neither ICAM nor nitration are involved in the retinal vascular defects in diabetes, although we have data using ICAM-1 knockout animals that argues against this conclusion.

It is clear that the drug did get to the retina, did exert biologic effects, and did demonstrate a significant ability of the drug to inhibit at least the early vascular lesions of diabetic retinopathy.

Sensory neuropathy: It has been postulated by others that advanced glycation endproducts (AGEs) and interaction of these AGEs with RAGE induce oxidative stress, upregulate NF-kB and various NF-kB-mediated proinflammatory genes in the nerves, and exaggerate neurological dysfunction, including altered pain sensation. The present data is consistent with evidence that RAGE-mediated signaling contributes to the development of at least some aspects of diabetic neuropathy, and provides evidence that the sRAGE-Ig fusion protein inhibits this process in long-term studies.

Example 3

Evaluation of a Rage-Ig Fusion Protein Using the Type II Collagen-Induced Arthritis Mouse Model Immunization of susceptible strains of mice with type II collagen, the major component of joint cartilage, induces a progressive, inflammatory arthritis (Wooley et al. *Journal of Experimental Medicine* 1981; 154:688-700). Collagen induced arthritis (CIA) is characterized clinically by erythema and edema, with affected paw width increases of typically 100%. A clinical scoring index has been developed to assess disease progression to joint distortion and spondylitis (Wooley *Methods In Enzymology* 1988; 162:361-373). Histopathology of affected joints reveals synovitis, pannus formation, and cartilage and bone erosion, which may also be represented by an index. Immunological laboratory findings include high antibody levels to type II collagen, and hypergammaglobulinemia. This model is now well established for testing of immunotherapeutic approaches to joint disease (Staines et al. *British Journal of Rheumatology* 1994; 33(9): 798-807), and has been successfully employed for the study of both biological and pharmacological agents for the treatment of rheumatoid arthritis (RA) (Wooley et al. *Arthritis Rheum* 1993; 36:1305-1314, and Wooley et al. *Journal of Immunology* 1993; 151:6602-6607).

Antagonism of the RAGE receptor is recognized as a potential therapeutic target in RA. Blockade of RAGE in mice with collagen-induced-arthritis resulted in the suppression of the clinical and histologic evidence of arthritis, and disease amelioration was associated with a reduction in the levels of TNFα-IL-6, and matrix metalloproteinases MMP-3, MMP-9 and MMP-13 in arthritic paw tissue (Hofmann et al. *Genes Immun* 2002; 3(3):123-135). This indicates that the collagen induced arthritis is sensitive to RAGE targeted therapy.

Figure 7:
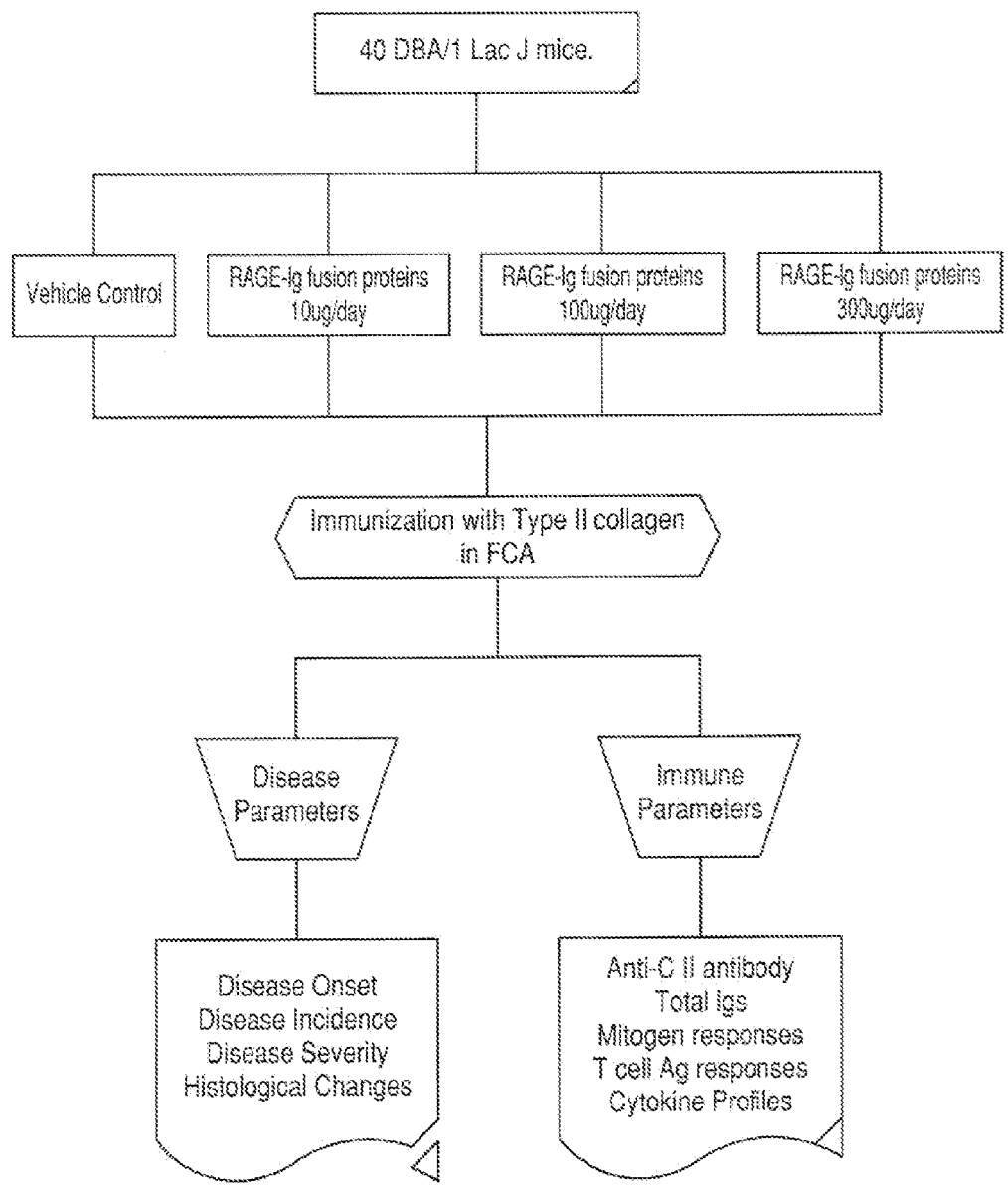
FIG. 7 provides a flow chart showing the experimental protocol of Example 3.

This experiment will evaluate the influence of RAGE-Ig fusion protein on CIA at three doses administered from the time of immunization with type II collagen. The study design is shown in FIG. 7.

Forty DBA/1 LacJ mice 8-10 weeks of age were obtained from Jackson Labs, and acclimatized in the facility for a minimum of 10 days prior to experimentation. All animals weighed>16 grams at the start of the experiment. Mice were divided into one of four treatment groups: 1) 100 µl sterile PBS by i.p. injection daily; 2) 100 µl sterile PBS containing RAGE-Ig fusion protein at 10 µg by i.p. injection daily; 3) 100 µl sterile PBS containing RAGE-Ig fusion protein at 100 µg by i.p. injection daily; and 4) 100 µl sterile PBS containing RAGE-Ig fusion protein at 300 µg by i.p. injection daily.

Three days after the initial dosing, all mice were injected with 100 µg bovine type II collagen in Freund's complete adjuvant (FCA) intradermally at the base of the tail. Mice were monitored by daily examination for the onset of disease, which was recorded. Mice were weighed weekly, and overall health status noted. Arthritis affected animals were clinically assessed five times per week until ten weeks after immunization, and paw measurements were made three times per week. Mice without signs of arthritis ten weeks after immunization were considered disease negative.

Results

Figure 8:
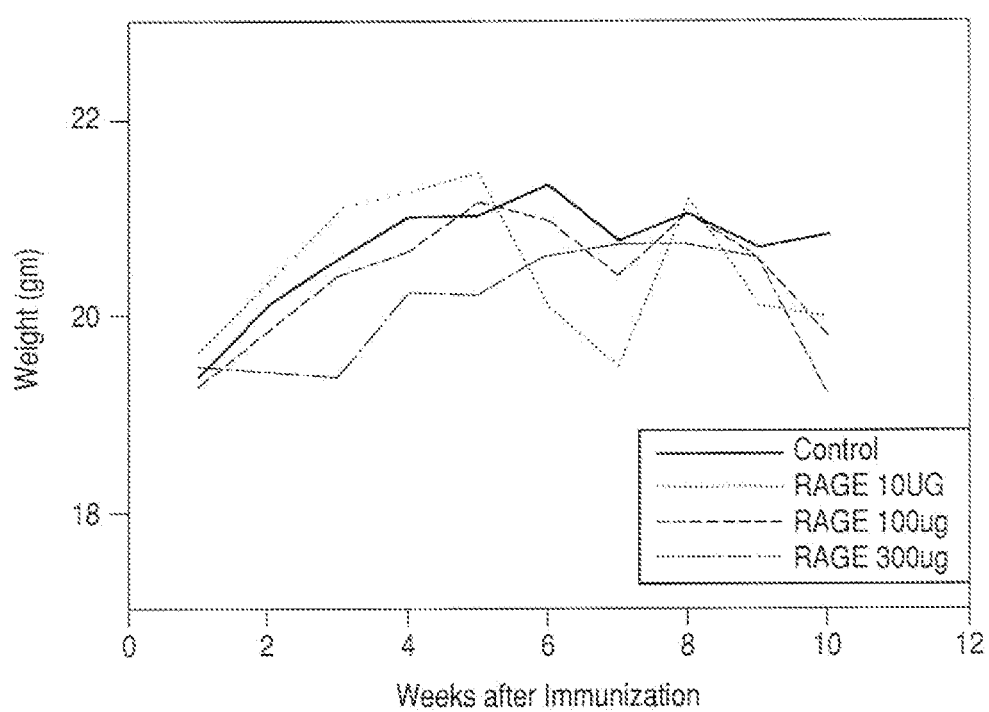
FIG. 8 is a line graph showing the effects of an exemplary RAGE-Ig fusion protein on test animal weights in a type-II collagen induced arthritis mouse model.

Overall Health and Toxicity. No acute toxic episodes occurred during the trial, and all animals survived the duration of the experiment. The treatment was well tolerated, and no adverse signs such as for matting or irritation were observed. The mouse weights (FIG. 8) indicate minor changes in weight over the course of the trial, which is typical due to transient weight loss in individual animals corresponding to the onset of disease. None of those variations between the groups reached statistical significance.

Figure 9:
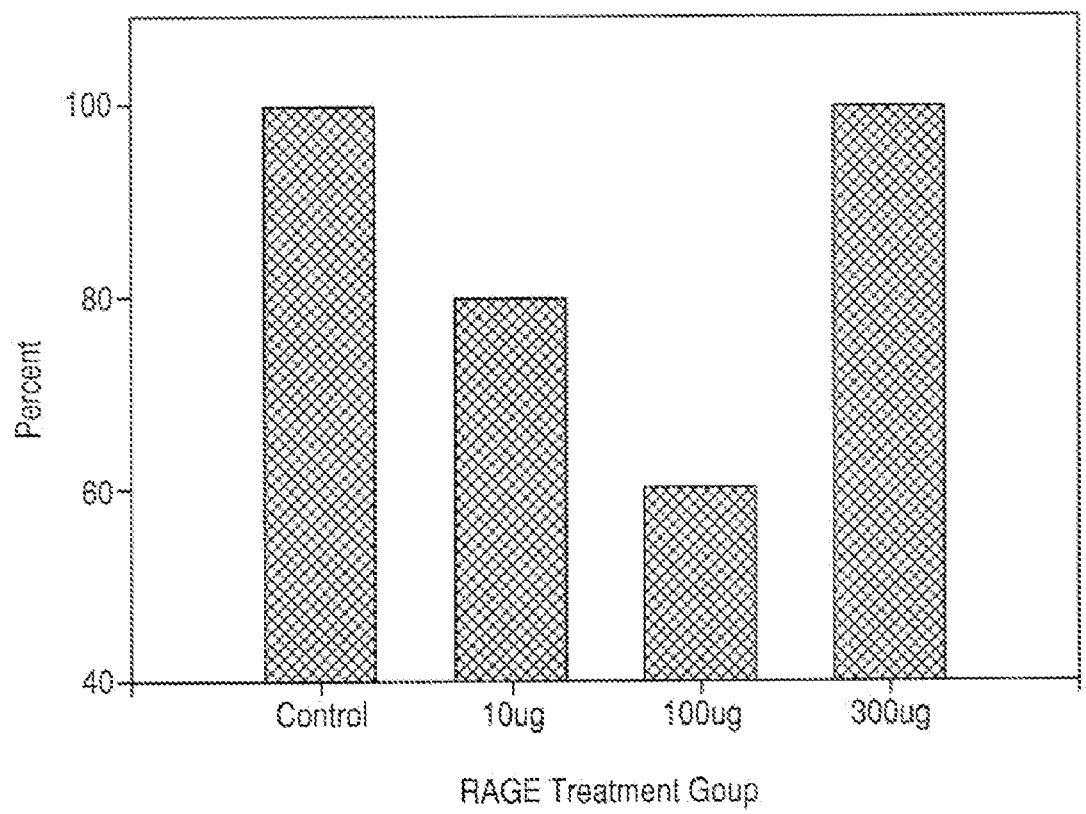
FIG. 9 is a bar graph showing the effects of an exemplary RAGE-Ig fusion protein on the incidence of arthritis in a type-II collagen induced arthritis mouse model.

Incidence and Onset of Arthritis. The terminal incidence of collagen arthritis in the trial is shown in FIG. 9. The control mice reached 100% onset, which is not unusual in classic collagen arthritis model, where the typical incidence ranges from 80%-100%. Mice treated with 10 µg day RAGE reached an incidence of 80%, which was not a significant reduction in incidence. Mice treated with 100 µg day RAGE exhibited a 60% incidence of arthritis, which was significantly lower than the control group (p<0.05). Surprising the incidence of arthritis in mice treated with 300 µg RAGE was 100%, and thus similar to the control incidence.

Figure 10:
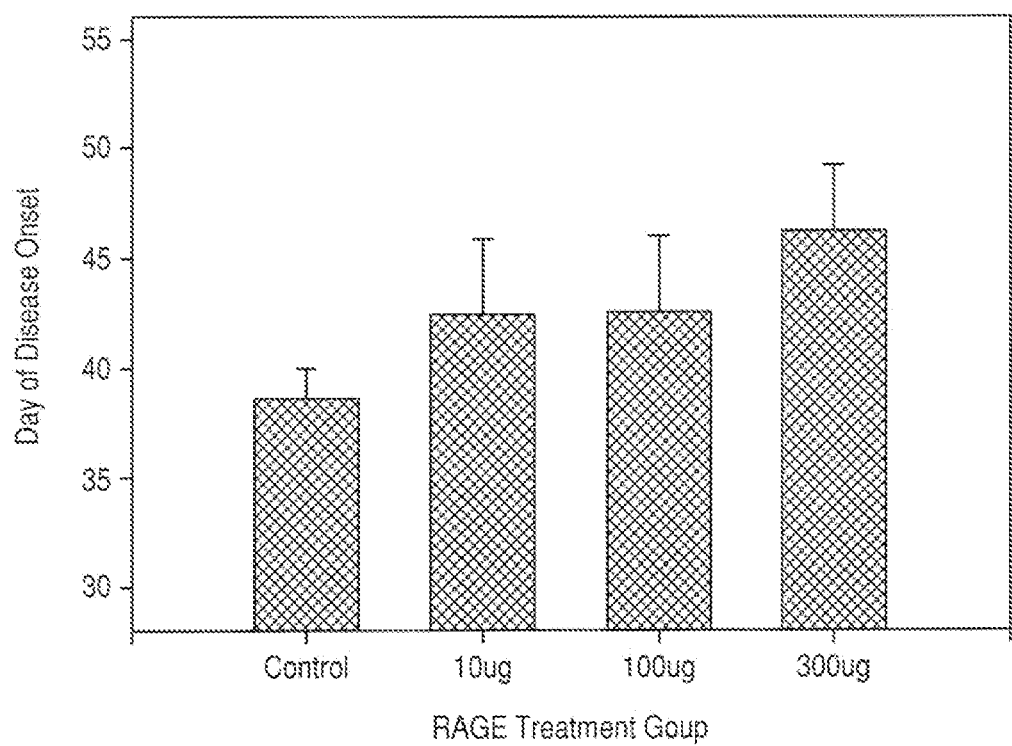
FIG. 10 is a bar graph, showing the effects of an exemplary RAGE-Ig fusion protein on the onset of arthritis in a type-II collagen induced arthritis mouse model.

The mean (and SEM) of the day of disease onset is shown in FIG. 10. Disease onset was typical in the control group, with a mean day with the first appearance of arthritis of 38.6. Disease onset in mice treated with either 10 µg or 100 µg RAGE was nominally delayed to 42.5, which did not achieved statistical significance. However, disease onset was significantly delayed (p<0.05) in mice treated with RAGE at 300 µg. Therefore, although mice at the high dose did not exhibit a reduction in disease incidence, the time to the development of clinically overt arthritis was markedly increased.

Figure 11:
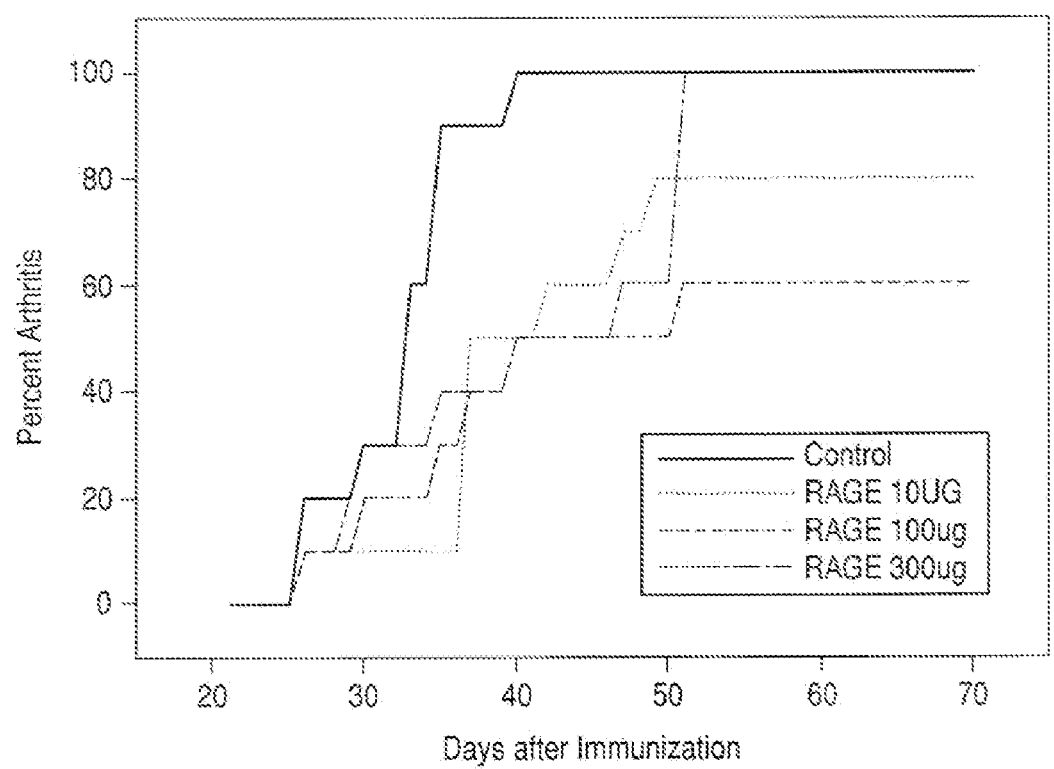
FIG. 11 is a line graph showing the effects of an exemplary RAGE-Ig fusion of protein on incidence of arthritis as a function of time in a type-II collagen induced arthritis mouse model.

The modulation of the onset of disease by RAGE treatment may be readily assessed by the plot of disease incidence over time (FIG. 11). The typical rapid disease onset characteristic of CIA is observed in the control group, while mice treated with RAGE at either 10 µg or 100 µg resulted in a delay of disease onset and a lower terminal incidence of arthritis. For approximately eight weeks, mice treated with 300 µg RAGE developed disease in a similar pattern, but a series of late arthritic animals resulted in a nigh disease incidence but delayed disease onset.

Figure 12:
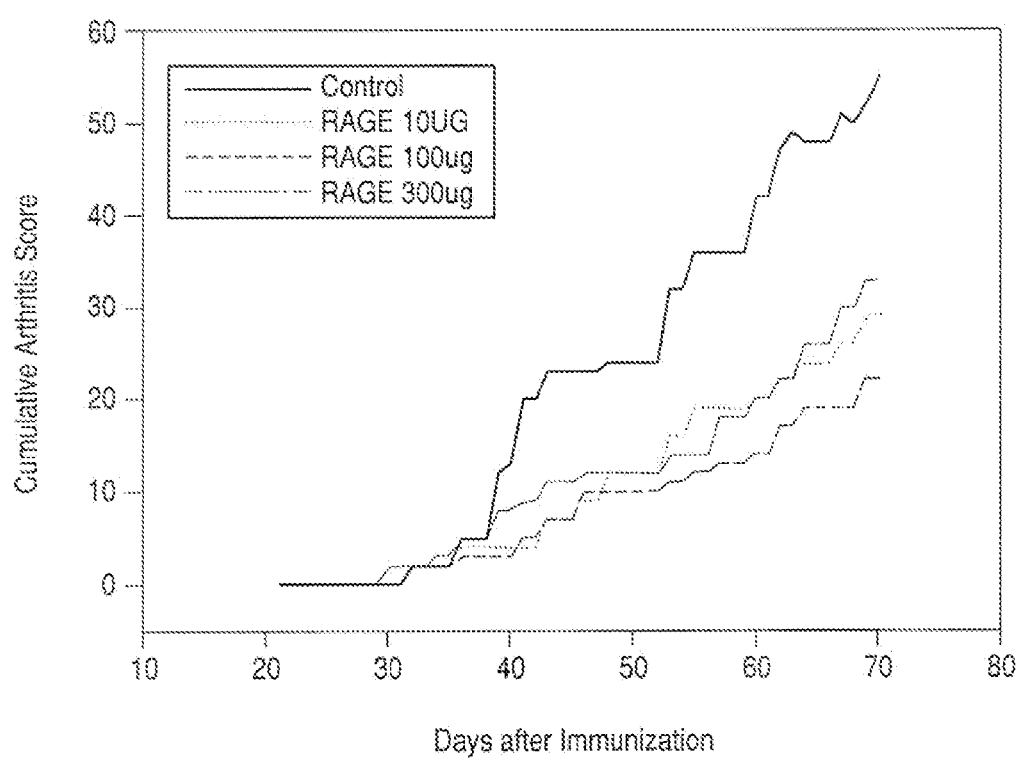
FIG. 12 is a line graph showing the effects of an exemplary RAGE-Ig fusion protein on the severity of arthritis as a function of time in a type-II collagen induced arthritis mouse model.

Disease Severity and Progression. Analysis of the cumulative joint score in treated and control animals revealed significant effects of RAGE therapy on the severity of collagen-induced arthritis (FIG. 12). Control mice developed the typical chronic progressing disease, with a marked increase in the cumulative arthritis index. In contrast, mice treated with RAGE at any dose exhibited a marked decrease in the arthritis score. The difference between the control and treated groups achieved a high level of statistical significance (p<0.001) from Day 43 post immunization, and this difference was maintained throughout the trial. Although RAGE therapy of 100 µg/day achieved the lowest arthritis cumulative score, there were no significant differences between the RAGE groups with respect to the arthritis score, suggesting that a 'threshold' effect was achieved, rather than a classic dose dependant effect.

Figure 13:
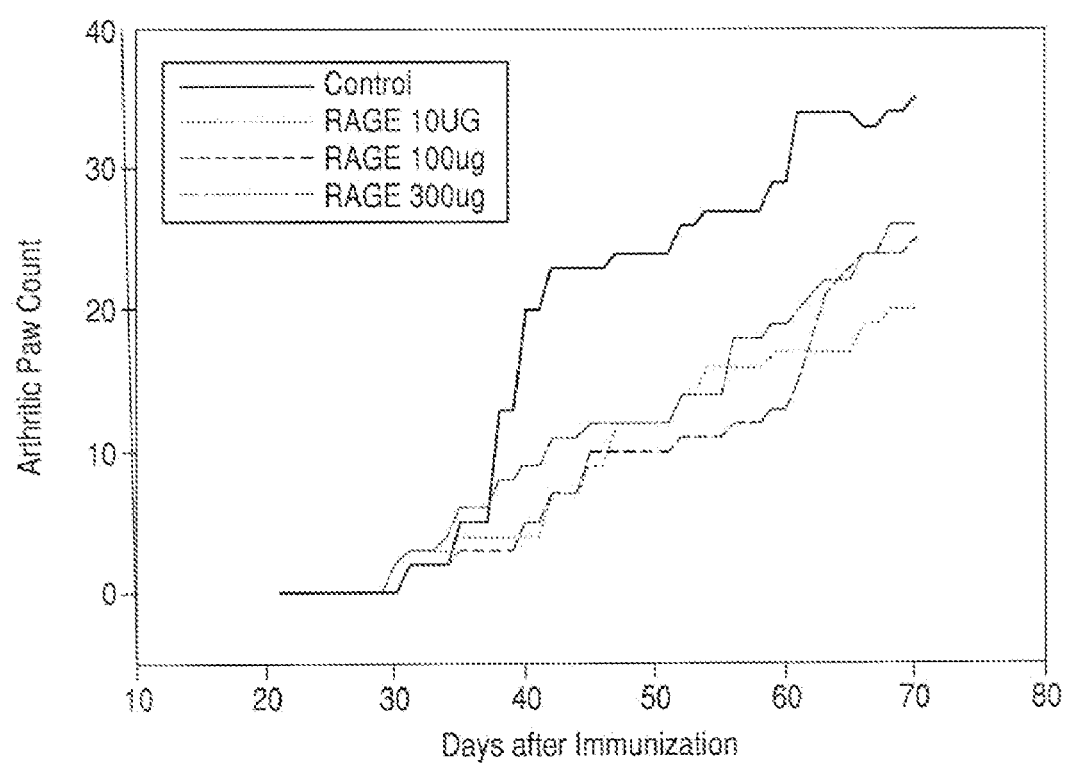
FIG. 13 is a line graph showing the effects of an exemplary RAGE-Ig fusion protein on the number of arthritic paws observed as a function of time in a type-II collagen induced arthritis mouse model.

The analysis on the influence of RAGE therapy on the number of arthritic paws (FIG. 13) does show a significant effect on the progression of the disease. Again, a significant influence was observed on the number of involved paws from Day 43 on. The level of significance varied from p<0.001 to p<0.025, which may reflect that the influence of RAGE was more pronounced upon disease severity than arthritis progression; however, the maximum number of involved paws (40) is more restricted than the maximum cumulative disease score (120). Again, there were no significant variations between the RAGE treated groups, although the 100 µg RAGE group did exhibit the highest level of retardation of arthritis.

The results suggest that administration of RAGE protein exerted a marked effect upon collagen-induced arthritis when administered using a prophylactic protocol. There were no overt toxic effects of RAGE injection at any dose, and the treatment appeared to be very well tolerated. The overall disease incidence was significantly reduced in mice receiving 100 µg daily, and a delay of disease onset was observed in mice treated with 300 µg/day. However, the most obvious indication of clinical activity was observed in the reduction of disease score and arthritic paw count, where a wide separation between RAGE treated mice and control animals was detected from Day 43 post immunization. At this point, control animals underwent the typical progression of severe arthritis, while RAGE treatment at all doses retarded the disease progression.

Histopathological assessment: Limbs from all mice were removed at the completion of the clinical assessment study, and stored in neutral buffered formalin solution. Joints were decalcified for 18 days in 10% formic acid, dehydrated, and embedded in paraffin blocks. Sections were cut along a longitudinal axis, mounted and stained with either hematoxylin and eosin or Toluidine Blue. Specimens were cut to approximately the mid line, and then sagital central samples mounted for evaluation. This allowed a consistent geographic evaluation. Five to ten samples were mounted (usually 4-6 samples per slide). After staining, the slides were permanently bonded with coverslips. A minimum of 3 separate sections per specimen were evaluated in a blinded fashion, with the evaluator unaware of the group assignment. On front limbs, all elbow, wrist, and metacarpal joints were scored, while all knee, ankle, and metatarsal joints were scored on the rear paws. Digits were not evaluated, since the sectioning procedure eliminates most PIP joints. Slides were evaluated for the presence of synovitis, pannus formation, marginal erosions, architectural changes (mostly subluxation), and destruction. Art overall score, based on these collective points, was then assigned to each section. The scoring system was based as follows:

Synovitis was judged by the thickness of the synovial membrane, and scored as follows: 0 for less than 3 cells thick;

1 for 3-5 cells thick; 2 for 6-10 cells thick; 3 for 10-20 cells thick; and 4 for 20-30 cells thick.

Pannus formation was scored as follows: 0 for no pannus formation; 1 for microvillus present; 2 for clear pannus attachment; 3 for marked pannus attachment; and 4 for joint space filled by pannus.

Marginal erosions were scored as follows: 0 for no erosions visible; 1 for minor indentation in area of capsular attachment; 2 for clear erosions of cartilage; 3 for erosions extend into subchondral bone; and 4 for major erosion of bone and cartilage.

Architectural changes were scored as follows: 0 for normal joint architecture; 1 for edematous changes; 2 for minor subluxation of articulating surfaces; 3 for major subluxation of articulating surfaces; 4 for complete fibrosis and collagen bridging.

The overall score reflects: 0 for classical normal joint appearance; 1 for minor changes; consistent with remission; may be clinically normal; 2 for definite inflammatory arthritis; 3 major inflammatory, erosive disease; and 4 for destructive, erosive arthritis.

Cartilage and Bone Matrix degradation. Serial sections were stained for cartilage matrix components using the histochemical stain Toluidine Blue. The toluidine blue sections were evaluated for proteoglycan loss. The staining at the articular surface was compared to staining at the growth plate, and was scored as follows: 0 for No proteoglycan loss; Normal Toluidine Blue staining; 1 for Minor proteoglycan loss; Some loss of staining from the superficial cartilage; 2 for Moderate proteoglycan loss; Weak staining of superficial cartilage; 3 for Significant proteoglycan loss; No Toluidine Blue staining of superficial cartilage; and 4 for Major proteoglycan loss; No Toluidine Blue staining of deep cartilage.

Results

Figure 14:
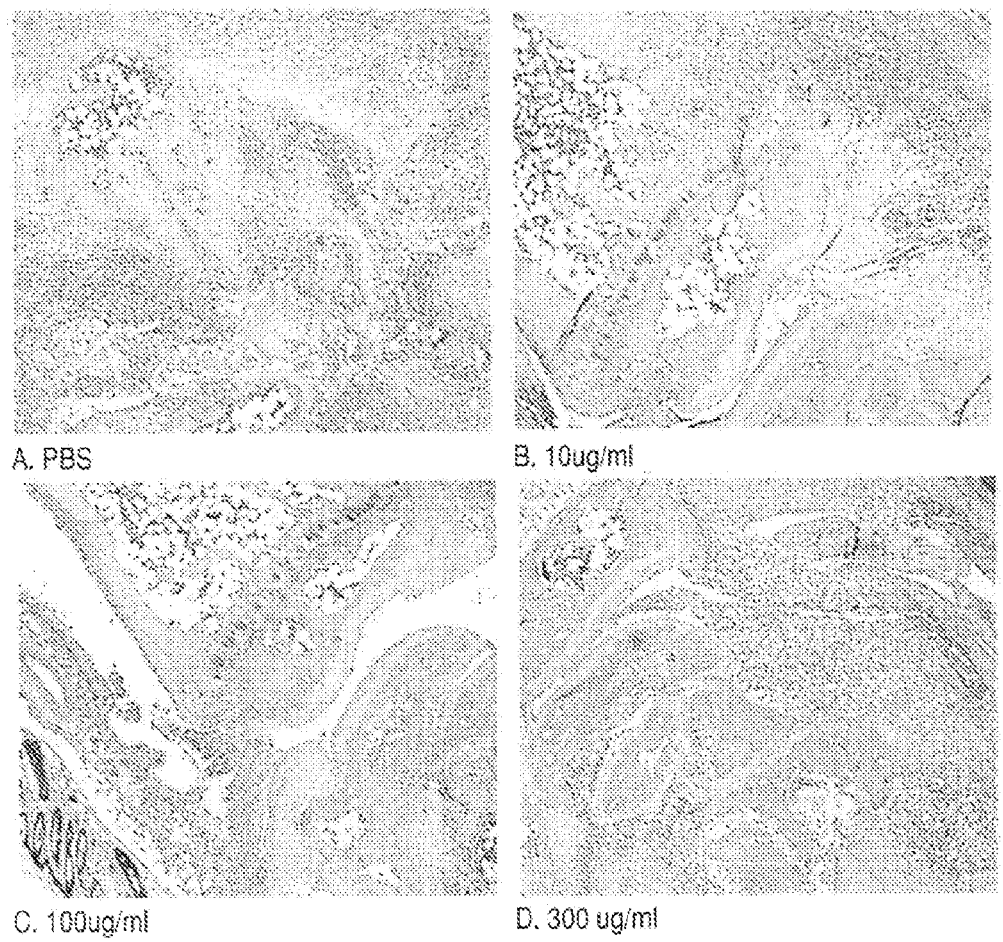
FIGS. 14A-14D are photomicrographs showing the effects of an exemplary RAGE-Ig fusion protein on joint morphology as a function of increasing amounts of the fusion protein in a type-II collagen induced arthritis mouse model.

Histological Findings of Collagen-induced arthritis. Sections were assessed for the inflammatory and erosive parameters of disease. The appearance of the arthritis (FIG. 14) reveals typical inflammatory erosive disease pathology for this time point in the control (PBS treated) group, with the typical arthritic features of synovial hypertrophy and hyperplasia, with marked pannus attachment and marginal erosions.

Treatment with the RAGE-Ig, fusion protein at 10 µg/ml (FIG. 14B) resulted in moderate changes in the inflammatory and erosive parameters, with an overall improvement in the appearance of erosions and disrupted cartilage surfaces. Treatment with the RAGE-Ig fusion protein at 100 µg/ml (FIG. 14C) resulted in a reduction in pannus formation and erosions compared with the control, and the overall difference was quite marked. However, administration of the RAGE-Ig fusion protein at 300 µg/ml (FIG. 14D) resulted in arthritis that appeared somewhat less severe than the pathology seen in the saline control, but was nevertheless quite severe, with synovial hypertrophy and hyperplasia, with marked pannus attachment and marginal erosions.

Figure 15:
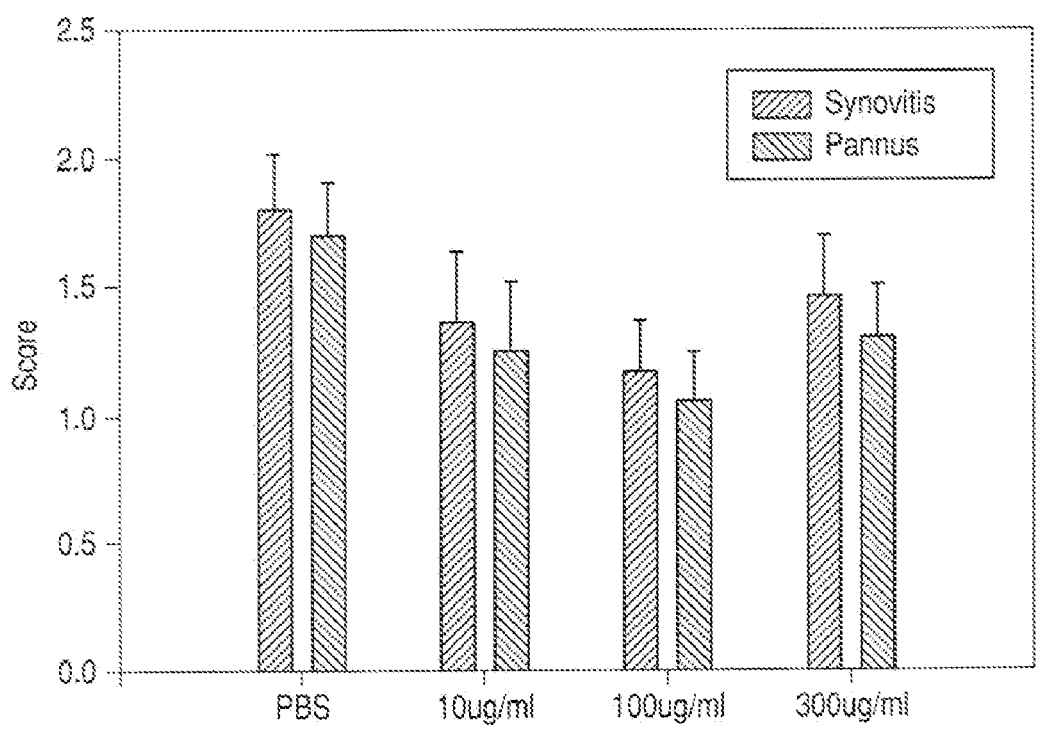
FIG. 15 is a bar graph showing the effects of an exemplary RAGE-Ig fusion protein on synovitis (black bars) and pannus (grey bars) in a type-II collagen induced arthritis mouse model.

Analysis of the inflammatory scores (FIG. 15) revealed a reduction in the inflammation in mice treated with the RAGE-Ig fusion protein at all doses when compared with control (saline-treated) animals. However the synovitis was significantly reduced ($p<0.05$) only in the 100 µg/ml group, and the pannus formation showed similar reductions in score ($p<0.03$). The reductions in the inflammatory disease parameters observed using the RAGE-Ig fusion protein at either 10 µg/ml or 300 µg/ml failed to reach statistical significance.

Figure 16:
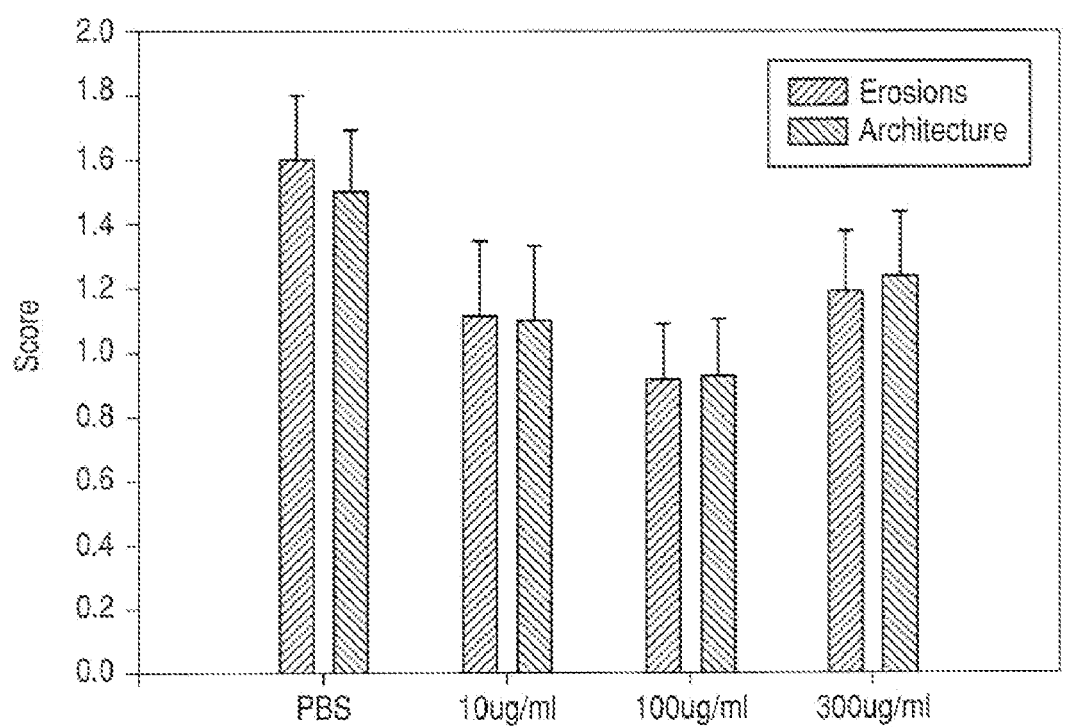
FIG. 16 is a bar graph showing the effects of an exemplary RAGE-Ig fusion protein on marginal erosion (black bars) and architectural changes (grey bars) in a type-II collagen induced arthritis mouse model.

Assessment of changes in the erosive features (erosions and changes in joint architecture) of collagen-induced arthritis showed a similar pattern of effects. A significant reduction ($p<0.01$) in joint erosions was observed between the group treated with the RAGE-Ig fusion protein at 100 µg/ml when compared with control (saline-treated) animals (FIG. 16), while the reductions observed in mice treated with the RAGE-Ig fusion protein at 10 µg/ml and 300 µg/ml did not reach significance.

Figure 17:
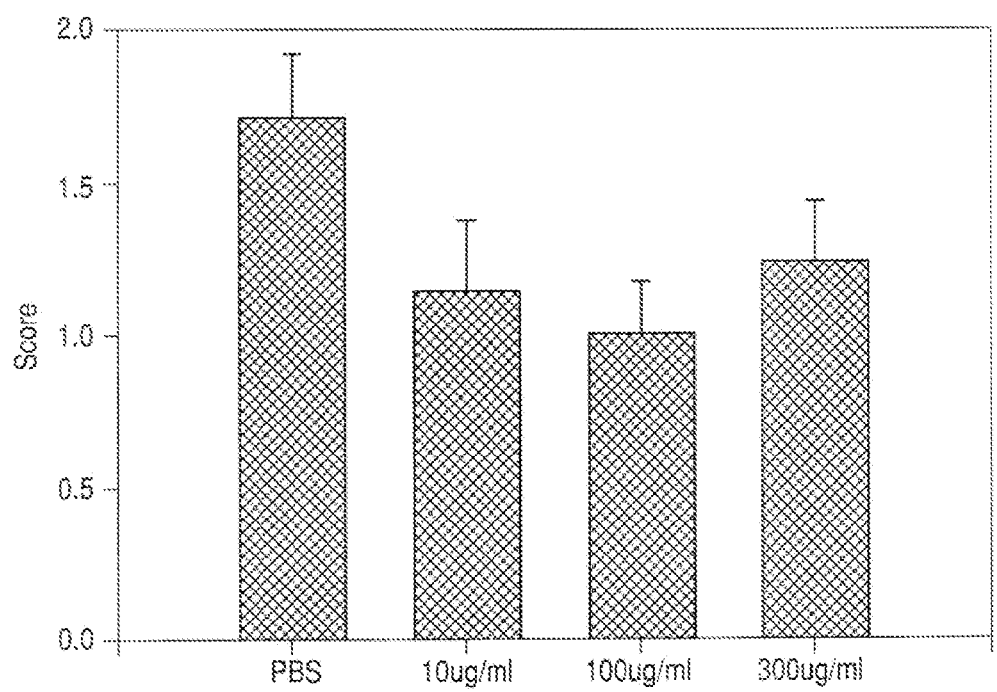
FIG. 17 is a bar graph showing the effects of an exemplary RAGE-Ig fusion protein on overall histological arthritis score in a type-II collagen induced arthritis mouse model.

The combination of the histopathological parameters into an overall histological arthritis score (FIG. 17) reflected the findings of the individual pathology parameters. Significant differences between the control (saline) treated animals and mice treated with the RAGE-Ig fusion protein at 100 µg/ml ($p<0.02$) were observed, and the overall score in mice treated at 10 µg/ml just achieved significance ($p=0.05$), while no significant reductions in the overall disease scores were observed using the RAGE-Ig fusion protein at 300 µg/ml.

Figure 18:
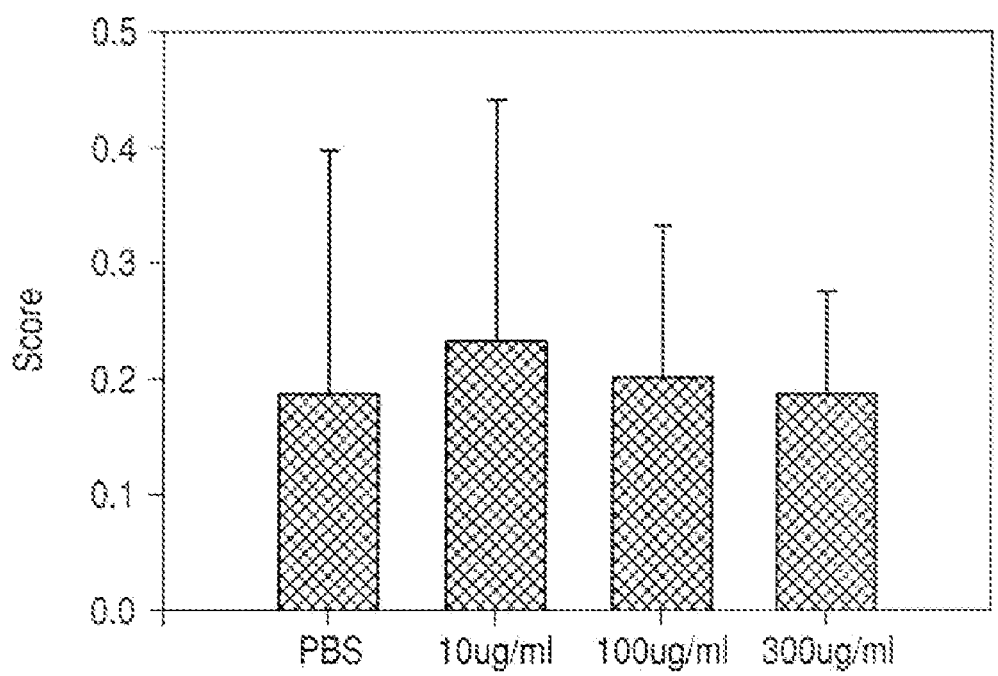
FIG. 18 is a bar graph showing the effects of an exemplary RAGE-Ig fusion protein on joint matrix protein loss in a type-II collagen induced arthritis mouse model.
Figure 19:
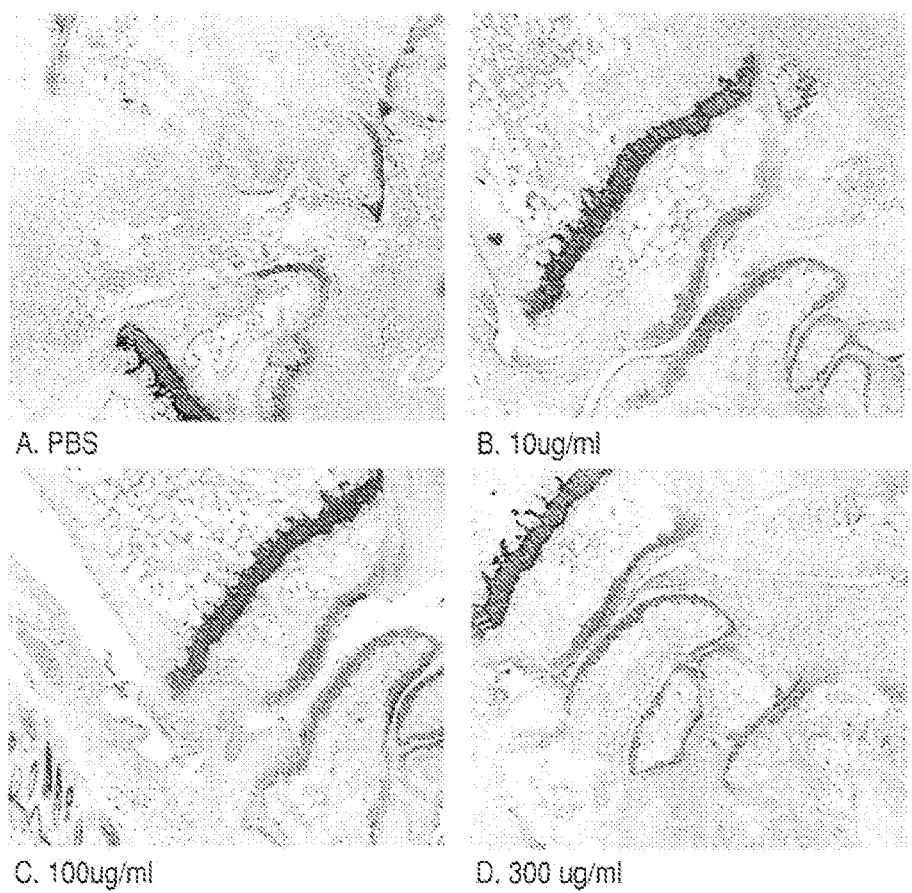
FIGS. 19A-19D are photomicrographs of toluidine blue stained sections showing the effects of an exemplary RAGE-Ig fusion protein on joint matrix protein loss in a type-II collagen induced arthritis mouse model.

The Toluidine Blue stained sections were examined to determine whether the RAGE-Ig fusion protein influenced the loss of matrix proteins from the arthritic joint. The data (shown in FIGS. 18 and 19) suggest that the RAGE-Ig fusion protein did protect against proteoglycan loss, but this effect was only statistically significant ($p<0.05$) at the 100 µg/ml dose. The PBS control group exhibits major loss of cartilage matrix (proteoglycans and collagens), and a marked loss of staining at the proximal cartilage surface is seen in mice treated with the RAGE-Ig fusion protein at 300 µg/ml. In contrast, there is good preservation of the matrix protein with administration of the RAGE-Ig fusion protein at 10 µg/ml or 100 µg/ml.

The histological findings confirm the clinical data that indicate that treatment of collagen-induced arthritis with the RAGE-Ig fusion protein resulted in an effect on the incidence and severity of the disease. The histological parameters reached high of levels statistical significance in once treated with 100 µg/ml, and achieved statistical significance on the overall pathology in mice treated with 10 µg/ml. RAGE-Ig fusion protein at 100 µg/ml achieved good preservation of the joint structure, and a significant reduction of all the parameters of arthritis under evaluation. The overall impression is that the RAGE-Ig fusion protein blocked the erosive phase of arthritis, since the degree of inflammatory changes was less influenced than the secondary disease parameters. Mice treated with the RAGE-Ig fusion protein at 300 µg/ml were not protected to the same degree as the lower doses, again raising the possibility of a suppressive response to this level of protein administration. Overall, these findings are in agreement with the clinical observations made in the study, and demonstrate that the RAGE-Ig fusion protein can exert an anti-arthritic effect.

While the invention has been described in detail, and with reference to specific embodiments thereof, it will be apparent to one of ordinary skill in the art that various changes and modifications can be made therein without departing from the spirit and scope thereof and such changes and modifications may be practiced within the scope of the appended claims. All patents and publications herein are incorporated by reference to the same extent as if each individual publication was specifically and individually indicated to be incorporated by reference in their entirety.

What is claimed is:

1. An isolated fusion protein comprising at least one polypeptide comprising:
   (a) a first amino acid sequence comprising an amino acid sequence selected from the group consisting of amino acids 1-301, amino acids 24-301, amino acids 1-344, or amino acids 24-344 of SEQ ID NO:6; and
   (b) a second amino acid sequence at least 95% identical to a human heavy chain immunoglobulin IgG4 constant domain or a fragment thereof.

2. The isolated fusion protein according to claim 1, further comprising a linker between the first amino acid sequence and the second amino acid sequence.

3. A pharmaceutical composition comprising the isolated fusion protein of claim 1 and a pharmaceutically acceptable carrier.

4. An isolated fusion protein comprising at least one polypeptide comprising:
   (a) a first amino acid sequence comprising amino acids 1-344 of SEQ ID NO: 6; and
   (b) a second amino acid sequence at least 95% identical to a human heavy chain immunoglobulin IgG4 constant domain or a fragment thereof.

5. The isolated fusion protein according to claim 4, wherein the fusion protein comprises an amino acid sequence selected from the group consisting of SEQ ID NO:6, and SEQ ID NO:8.

6. The isolated fusion protein according to claim 5, wherein the fusion protein comprises the amino acid sequence of SEQ ID NO:6.

7. The isolated fusion protein according to claim 5, wherein the fusion protein comprises the amino acid sequence of SEQ ID NO:8.

8. The isolated fusion protein according to claim 4, wherein the amino acid sequence of the fusion protein consists of SEQ ID NO:6.

9. A pharmaceutical composition comprising the isolated fusion protein of claim 4 and a pharmaceutically acceptable carrier.

* * * * *

UNITED STATES PATENT AND TRADEMARK OFFICE
CERTIFICATE OF CORRECTION

PATENT NO.        : 8,398,977 B2                                    Page 1 of 1
APPLICATION NO.   : 12/664111
DATED             : March 19, 2013
INVENTOR(S)       : Bleck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 490 days.

Signed and Sealed this

First Day of September, 2015

Michelle K. Lee
*Director of the United States Patent and Trademark Office*